US011351545B2

United States Patent
Pryor et al.

(10) Patent No.: US 11,351,545 B2
(45) Date of Patent: Jun. 7, 2022

(54) HIGH SPEED NUCLEIC ACID MELTING ANALYSIS

(71) Applicants: Canon U.S.A., Inc., Melville, NY (US); University of Utah Research Foundation, Salt Lake City, UT (US)

(72) Inventors: Robert J. Pryor, Midvale, UT (US); Carl T. Wittwer, Salt Lake City, UT (US); Scott O. Sundberg, Yorktown, VA (US); Ivor T. Knight, Erie, PA (US); Joseph T. Myrick, West Point, VA (US); Robert A. Palais, Salt Lake City, UT (US); Jeanette Y. Paek, Los Alamitos, CA (US)

(73) Assignees: Canon U.S.A., Inc., Melville, NY (US); University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 15/664,843

(22) Filed: Jul. 31, 2017

(65) Prior Publication Data

US 2018/0111125 A1 Apr. 26, 2018

Related U.S. Application Data

(60) Provisional application No. 62/530,481, filed on Jul. 10, 2017, provisional application No. 62/503,550, filed on May 9, 2017, provisional application No. 62/368,435, filed on Jul. 29, 2016.

(51) Int. Cl.
| | | |
|---|---|---|
| *C12Q 1/6827* | (2018.01) | |
| *B01L 3/00* | (2006.01) | |
| *C12Q 1/68* | (2018.01) | |
| *B01L 7/00* | (2006.01) | |
| *C12Q 1/6806* | (2018.01) | |

(52) U.S. Cl.
CPC ..... *B01L 3/502784* (2013.01); *B01L 3/50851* (2013.01); *B01L 7/52* (2013.01); *C12Q 1/68* (2013.01); *C12Q 1/6806* (2013.01); *C12Q 1/6827* (2013.01)

(58) Field of Classification Search
CPC ...... C12Q 1/68; C12Q 1/6827; C12Q 1/6806; C12Q 1/6816; C12Q 1/686; C12Q 2523/305; C12Q 2527/101; C12Q 2527/107; C12Q 2537/165; B01L 3/502784; B01L 7/52; B01L 3/50851
See application file for complete search history.

(56) References Cited

U.S. PATENT DOCUMENTS

| | | | | |
|---|---|---|---|---|
| 2007/0026421 | A1* | 2/2007 | Sundberg | B01L 3/5027 435/6.12 |
| 2013/0122493 | A1 | 5/2013 | Xu et al. | |
| 2014/0039802 | A1 | 2/2014 | Kanderian | |
| 2014/0302501 | A1 | 10/2014 | Xu et al. | |
| 2015/0248524 | A1 | 9/2015 | Cobb et al. | |

FOREIGN PATENT DOCUMENTS

| | | |
|---|---|---|
| EP | 1 362 928 A2 | 11/2003 |
| JP | 2009-525759 A | 7/2009 |
| JP | 2012-523645 A | 10/2012 |
| JP | 2014-533506 A | 12/2014 |
| WO | 2015/071338 A1 | 5/2015 |

OTHER PUBLICATIONS

Pryor et al. Clinical Chemistry 2017; 63: 1624-1632. (Year: 2017).*
Sundberg et al. Clinical Chemistry 2014; 60: 1306-1313 (Year: 2014).*
Zhou et al. High-Resolution DNA Melting Analysis for Simultaneous Mutation Scanning and Genotyping in Solution. Clinical Chemistry 2005; 51: 1770-1777 (Year: 2005).*
Li et al. Genotyping Accuracy of High-Resolution DNA Melting Instruments. Clinical Chemistry 2014; 60: 864-872 (Year: 2014).*
Montgomery et al. Simultaneous Mutation Scanning and Genotyping by High-Resolution DNA Melting Analysis. Nature Protocols 2007; 2: 59-66 (Year: 2007).*
Perreault et al. Comparison of Genotype Clustering Tools with Rare Variants. BMC Bioinformatics 2014; 14: 52 (Year: 2014).*
Pryor et al. "High-Speed Melting Analysis: The Effect of Melting Rate on Small Amplicon Microfluidic Genotyping," Clinical Chemistry 63.10 (Oct. 1, 2017) pp. 1624-1632. Only abstract available.
Tianlan Chen et al., "Sub-7-second genotyping of single-nucleotide polymorphism by high-resolution melting curve analysis on a thermal digital microfluidic device", Lab Chip, 2016,16, 743-752.

* cited by examiner

*Primary Examiner* — Angela M. Bertagna
(74) *Attorney, Agent, or Firm* — Rothwell, Figg, Ernst & Manbeck, P.C.

(57) ABSTRACT

A method and system have been provided to perform high speed nucleic acid melting analysis while still obtaining accurate melting curve sufficient for genotyping. This rapid ability to interrogate DNA should be useful whenever time to result is important, such as in molecular point of care testing. Specifically, microfluidics enables genotyping by melting analysis at rates up to 50° C./s, requiring less than is to acquire an entire melting curve. High speed melting reduces the time for melting analysis, decreases errors, and improves genotype discrimination of small amplicons.

14 Claims, 20 Drawing Sheets
(13 of 20 Drawing Sheet(s) Filed in Color)
Specification includes a Sequence Listing.

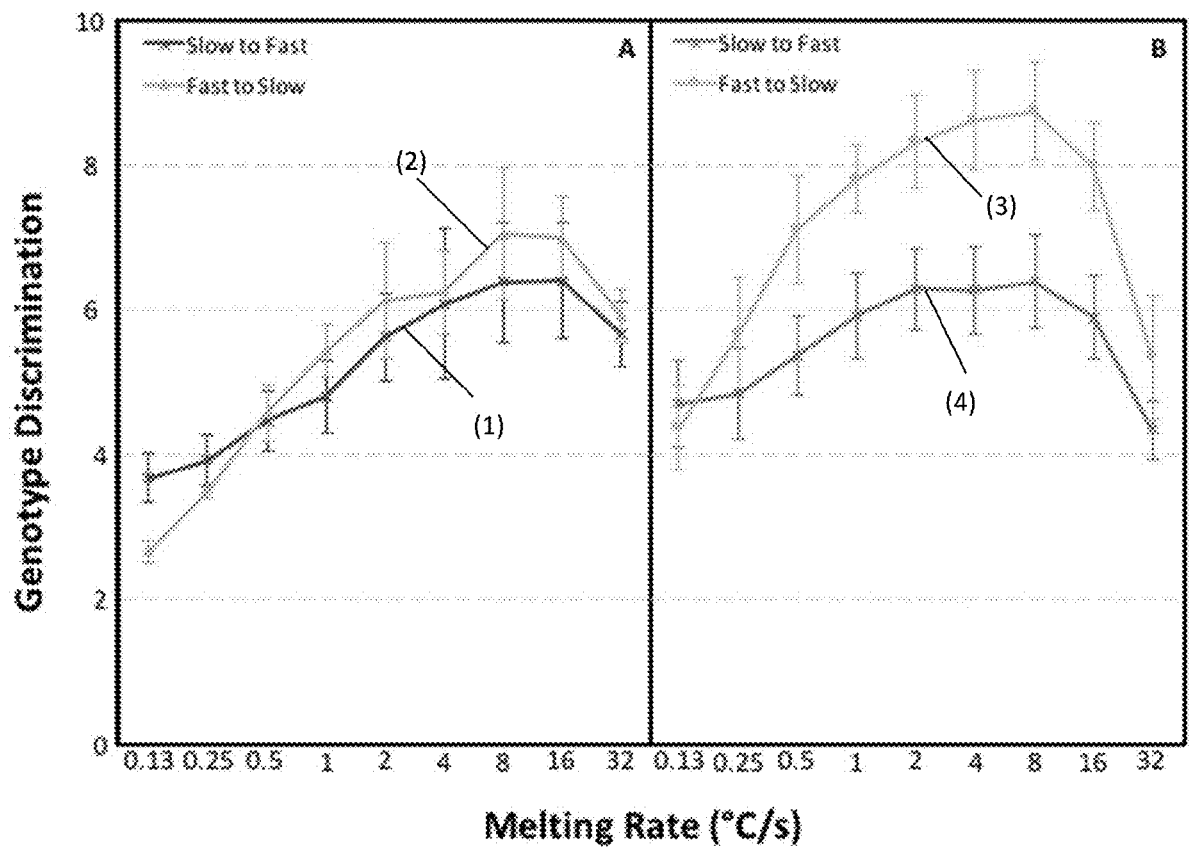
FIGs. 19A-B

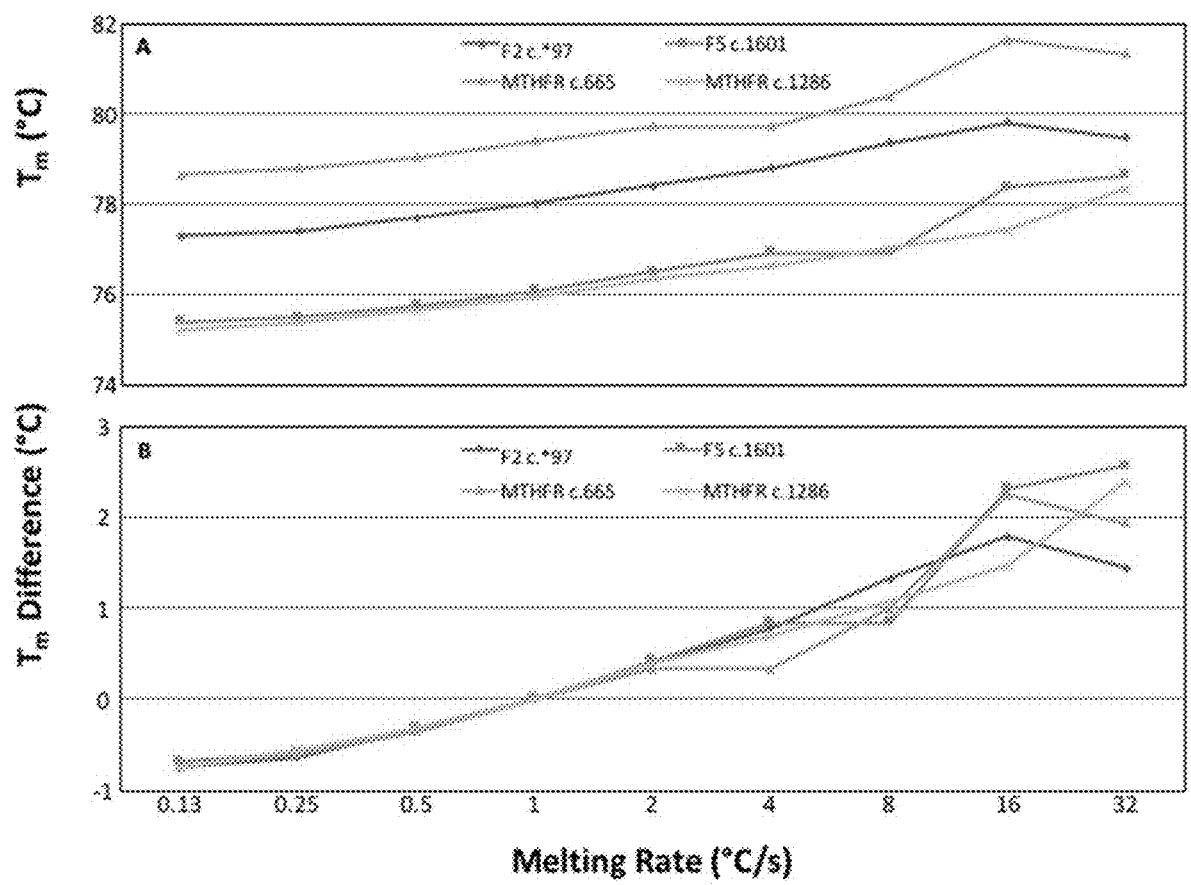
FIGs. 20A-B

Table 4:
Blinded Study PCR Conditions

| Target | Primer 1 | Primer 2 | Initial Denaturation | Denaturation (°C, s) | Annealing (°C, s) | Extension (°C, s) | Cycles |
|---|---|---|---|---|---|---|---|
| HFE c.187C>G | SEQ ID NO: 19 TGGGCTACGTGGATGA | SEQ ID NO: 20 AAACCCATGGAGTTCGG | 94, 10 | 94, 1 | 60, 1 | 72, 2 | 40 |
| CPS1 c. 3405-29A>T | SEQ ID NO: 21 AGTCAAGTCTAGTATTAGCATAAACCT | SEQ ID NO: 22 AAGGAAGGGGAAAAAAGCAG | 95, 120 | 95, 10 | 65, 10 | 72, 10 | 35 |
| | ATAGGTTGTCTGGAACTGTTCTGTTGGTTGATTGTCCTGTGA | TCATAGCAGACCCACTGGAA CAGTCACTACAAAGAAATTGGACA | 95, 120 95, 120 | 95, 10 95, 15 | 65, 15 65, 15 | 72, 15 72, 15 | 35 40 |
| M13 phage | SEQ ID NO: 23 GCATTTGAGGGGGATTCAATGA | SEQ ID NO: 24 CAATACTGCGGAATCGTCATAAATA | 95, 10 | 95, 1 | 61, 1 | 72, 2 | 40 |
| | TCATTCTCGTTTTCTGAACTG TCATTCTCGTTTTCTGAACTG | ATGTTTAGACTGGATAGCGT AAAATAGCGAGAGCTTTGC | 95, 10 95, 10 | 95, 1 95, 1 | 58, 1 62, 1 | 72, 3 72, 6 | 40 40 |
| pBR322 plasmid | SEQ ID NO: 25 CGGAATCTTGCACGCCCT ATGATGGCCTGTGCTTGC ATGGCCTGCTTCTCGCGAA | SEQ ID NO: 26 GGTGGCGGGACCAGTG AGCGCTCTGGGTCATTTCG CGAACGCCAGCAAGAGCGTAG | 95, 10 95, 10 95, 10 | 95, 1 95, 1 95, 1 | 65, 1 68, 1 66, 1 | 72, 2 72, 3 72, 6 | 35 40 40 |

FIG. 21

Table 5: Blind Text Result

| Correct manual genotype calls (°C/s) SNV | Amplicon Size (bp) | %GC | Tm (°C) | SNV Class | Heterozygote | Homozygote | Nearest Neighbor Symmetric | Rate is Better |
|---|---|---|---|---|---|---|---|---|
| HFE c.187C>G | 78 | 55 | 88 | 3 | 0.13 – 32 | None | Yes | fast |
| CPS1 c. 3405-29A>T | 51 | 39 | 76 | 4 | 0.13 – 32 | 0.13 – 32 | Yes | fast |
|  | 100 | 43 | 83 | 4 | 0.13 – 32 | None | Yes |  |
|  | 272 | 42 | 86 | 4 | None | None | Yes |  |
| M13 phage A>T | 96 | 38 | 82 | 4 | 0.13 – 16 | None | Yes | slow |
|  | 210 | 38 | 84 | 4 | None | None | Yes |  |
| M13 phage G>C | 96 | 38 | 82 | 3 | 0.13 – 32 | None | Yes | slow |
|  | 210 | 38 | 84 | 3 | 0.13 – 1 | None | Yes |  |
| pBR322 plasmid A>T | 101 | 59 | 91 | 4 | 0.13 – 32 | None | No | slow |
|  | 200 | 64 | 95 | 4 | None | None | No |  |
| pBR322 plasmid G>C | 101 | 59 | 91 | 3 | 0.13 – 32 | None | No | fast |
|  | 200 | 64 | 95 | 3 | 0.5 – 8 | None | No |  |
| M13 phage A>C | 48 | 40 | 75 | 2 | 0.25 – 32 | 0.13 – 32 | No | fast |
|  | 96 | 38 | 82 | 2 | 0.13 – 16 | 0.13 – 32 | No |  |
|  | 210 | 38 | 84 | 2 | None | None | No |  |
| M13 phage A>C | 49 | 65 | 87 | 2 | 0.5 – 32 | 0.5 – 32 | No | slow |
|  | 101 | 59 | 91 | 2 | 0.25 – 32 | 0.25 – 1 | No |  |
|  | 200 | 64 | 95 | 2 | 0.25 – 4 | 0.5 – 4 | No |  |

FIG. 22

```
                             SEQUENCE LISTING

<160> NUMBER OF SEQ ID NOS: 26

<210> SEQ ID NO 1
<211> LENGTH: 24
<212> TYPE: DNA
<213> ORGANISM: Artificial Sequence
<220> FEATURE:
<223> OTHER INFORMATION: Primer F2 c.*97G>A

<400> SEQUENCE: 1
gttcccaata aaagtgactc tcag                                           24

<210> SEQ ID NO 2
<211> LENGTH: 19
<212> TYPE: DNA
<213> ORGANISM: Artificial Sequence
<220> FEATURE:
<223> OTHER INFORMATION: Primer F2 c.*97G>A reverse

<400> SEQUENCE: 2
tagcactggg agcattgag                                                 19

<210> SEQ ID NO 3
<211> LENGTH: 17
<212> TYPE: DNA
<213> ORGANISM: Artificial Sequence
<220> FEATURE:
<223> OTHER INFORMATION: Primer F5 c.1601G>A Forward

<400> SEQUENCE: 3
gcagatccct ggacagg                                                   17

<210> SEQ ID NO 4
<211> LENGTH: 22
<212> TYPE: DNA
<213> ORGANISM: Artificial Sequence
<220> FEATURE:
<223> OTHER INFORMATION: Primer F5 c.1601G>A reverse

<400> SEQUENCE: 4
caaggacaaa atacctgtat tc                                             22

<210> SEQ ID NO 5
<211> LENGTH: 20
<212> TYPE: DNA
```

```
<213> ORGANISM: Artificial Sequence
<220> FEATURE:
<223> OTHER INFORMATION: Primer MTHFR c.665C>T Forward

<400> SEQUENCE: 5
ttgaaggaga aggtgtctgc                                          20

<210> SEQ ID NO 6
<211> LENGTH: 20
<212> TYPE: DNA
<213> ORGANISM: Artificial Sequence
<220> FEATURE:
<223> OTHER INFORMATION: Primer MTHFR c.665C>T Reverse

<400> SEQUENCE: 6
aagctgcgtg atgatgaaat                                          20

<210> SEQ ID NO 7
<211> LENGTH: 19
<212> TYPE: DNA
<213> ORGANISM: Artificial Sequence
<220> FEATURE:
<223> OTHER INFORMATION: Primer MTHFR c.1286A>C Forward

<400> SEQUENCE: 7
ggaggagctg accagtgaa                                           19

<210> SEQ ID NO 8
<211> LENGTH: 25
<212> TYPE: DNA
<213> ORGANISM: Artificial Sequence
<220> FEATURE:
<223> OTHER INFORMATION: Primer MTHFR c.1286A>C Reverse

<400> SEQUENCE: 8
aagaacgaag acttcaaaga cactt                                    25

<210> SEQ ID NO 9
<211> LENGTH: 46
<212> TYPE: DNA
<213> ORGANISM: Artificial Sequence
<220> FEATURE:
<223> OTHER INFORMATION: Internal Temp Control Forward
<220> FEATURE:
<221> NAME/KEY: misc_feature
<222> LOCATION: (46)..(46)
<223> OTHER INFORMATION: n is any nucleotide

<400> SEQUENCE: 9
ttgggcccct ccgacacgag ccccggctag cctgcatcct gccagn             46

<210> SEQ ID NO 10
<211> LENGTH: 46
<212> TYPE: DNA
<213> ORGANISM: Artificial Sequence
<220> FEATURE:
<223> OTHER INFORMATION: Internal Temp Control Reverse
<220> FEATURE:
<221> NAME/KEY: misc_feature
<222> LOCATION: (46)..(46)
<223> OTHER INFORMATION: n is any nucleotide

<400> SEQUENCE: 10
ctggcaggat gcaggctagc cggggctcgt gtcggagggg cccaan             46

<210> SEQ ID NO 11
<211> LENGTH: 35
```

```
<212> TYPE: DNA
<213> ORGANISM: Artificial Sequence
<220> FEATURE:
<223> OTHER INFORMATION: Low Tm Calibrator Forward

<400> SEQUENCE: 11
atcgtgattt ctatagttat ctaagtcgtt atata                              35

<210> SEQ ID NO 12
<211> LENGTH: 35
<212> TYPE: DNA
<213> ORGANISM: Artificial Sequence
<220> FEATURE:
<223> OTHER INFORMATION: Low Tm Calibrator Reverse

<400> SEQUENCE: 12
tatataacga cttagataac tatagaaatc acgat                              35

<210> SEQ ID NO 13
<211> LENGTH: 45
<212> TYPE: DNA
<213> ORGANISM: Artificial Sequence
<220> FEATURE:
<223> OTHER INFORMATION: High Tm Calibrator Forward

<400> SEQUENCE: 13
ttgcggtggg ccacggcgcg gcggcagcgc ttcgcttctg cgcca                   45

<210> SEQ ID NO 14
<211> LENGTH: 45
<212> TYPE: DNA
<213> ORGANISM: Artificial Sequence
<220> FEATURE:
<223> OTHER INFORMATION: High Tm Calibrator Reverse

<400> SEQUENCE: 14
tggcgcagaa gcgaagcgct gccgccgcgc cgtggcccac cgcaa                   45

<210> SEQ ID NO 15
<211> LENGTH: 201
<212> TYPE: DNA
<213> ORGANISM: Artificial Sequence
<220> FEATURE:
<223> OTHER INFORMATION: Template F2.*97G>A
<220> FEATURE:
<221> NAME/KEY: misc_feature
<222> LOCATION: (101)..(101)
<223> OTHER INFORMATION: n is G or A

<400> SEQUENCE: 15 gtaggggggcc actcatattc tgggctcctg gaaccaatcc cgtgaaagaa ttattttttgt  60 gtttctaaaa ctatggttcc caataaaagt gactctcagc nagcctcaat gctcccagtg  120
ctattcatgg gcagctctct gggctcagga agagccagta atactactgg ataaagaaga  180
cttaagaatc caccacctgg t                                             201

<210> SEQ ID NO 16
<211> LENGTH: 201
<212> TYPE: DNA
<213> ORGANISM: Artificial Sequence
<220> FEATURE:
<223> OTHER INFORMATION: Template F5 c.1601G>A
<220> FEATURE:
<221> NAME/KEY: misc_feature
<222> LOCATION: (101)..(101)
<223> OTHER INFORMATION: n is G or A
```

<400> SEQUENCE: 16
ttaacaagac catactacag tgacgtggac atcatgagag acatcgcctc tgggctaata    60
ggactacttc taatctgtaa gagcagatcc ctggacaggc naggaataca ggtattttgt   120
ccttgaagta acctttcaga aattctgaga atttcttctg gctagaacat gttaggtctc   180
ctggctaaat aatggggcat t                                              201

<210> SEQ ID NO 17
<211> LENGTH: 200
<212> TYPE: DNA
<213> ORGANISM: Artificial Sequence
<220> FEATURE:
<223> OTHER INFORMATION: Template MTHFR c.665C>T
<220> FEATURE:
<221> NAME/KEY: misc_feature
<222> LOCATION: (101)..(101)
<223> OTHER INFORMATION: n is C or T

<400> SEQUENCE: 17
tgactgtcat ccctattggc aggttacccc aaaggccacc ccgaagcagg gagctttgag    60
gctgacctga agcacttgaa ggagaaggtg tctgcgggag ncgatttcat catcacgcag   120
cttttctttg aggctgacac attcttccgc tttgtgaagg catgcaccga catgggcatc   180
acttgcccca tcgtccccgg                                                200

<210> SEQ ID NO 18
<211> LENGTH: 201
<212> TYPE: DNA
<213> ORGANISM: Artificial Sequence
<220> FEATURE:
<223> OTHER INFORMATION: Template MTHFRc.1286A>C
<220> FEATURE:
<221> NAME/KEY: misc_feature
<222> LOCATION: (101)..(101)
<223> OTHER INFORMATION: n is A or C

<400> SEQUENCE: 18
gcctttgggg agctgaagga ctactacctc ttctacctga gagcaagtc ccccaaggag    60 gagctgctga agatgtgggg ggaggagctg accagtgaag naagtgtctt tgaagtcttc   120
gttctttacc tctcgggaga accaaaccgg aatggtcaca aagtgagtga tgctggagtg   180
gggaccctgg ttcatcccct g                                              201

<210> SEQ ID NO 19
<211> LENGTH: 16
<212> TYPE: DNA
<213> ORGANISM: Artificial Sequence
<220> FEATURE:
<223> OTHER INFORMATION: Primer 1 for HFE c.187C>G

<400> SEQUENCE: 19
tgggctacgt ggatga                                                     16

<210> SEQ ID NO 20
<211> LENGTH: 17
<212> TYPE: DNA
<213> ORGANISM: Artificial Sequence
<220> FEATURE:
<223> OTHER INFORMATION: Primer 2 for HFE c.187C>G

<400> SEQUENCE: 20
aaacccatgg agttcgg                                                    17

```
<210> SEQ ID NO 21
<211> LENGTH: 70
<212> TYPE: DNA
<213> ORGANISM: Artificial Sequence
<220> FEATURE:
<223> OTHER INFORMATION: Primer 1 for CPS1 c.3405-29A>T

<400> SEQUENCE: 21
agtcaagtct agtattagca taaacctata ggttgtctgg aactgttctg ttggttgatt    60
gtcctggtga                                                          70

<210> SEQ ID NO 22
<211> LENGTH: 65
<212> TYPE: DNA
<213> ORGANISM: Artificial Sequence
<220> FEATURE:
<223> OTHER INFORMATION: Primer 2 for CPS1 c.3405-29A>T

<400> SEQUENCE: 22
aaggaagggg aaaaaaagca gtcatagcag acccactgga acagtcacta caaagaaatt    60
ggaca                                                               65

<210> SEQ ID NO 23
<211> LENGTH: 63
<212> TYPE: DNA
<213> ORGANISM: Artificial Sequence
<220> FEATURE:
<223> OTHER INFORMATION: Primer 1 for M13 phage

<400> SEQUENCE: 23
gcatttgagg gggattcaat gatcattctc gttttctgaa ctggcaatcc gctttgcttc    60
tga                                                                 63

<210> SEQ ID NO 24
<211> LENGTH: 66
<212> TYPE: DNA
<213> ORGANISM: Artificial Sequence
<220> FEATURE:
<223> OTHER INFORMATION: Primer 2 for M13 phage

<400> SEQUENCE: 24
caatactgcg gaatcgtcat aaataatgtt tagactggat agcgtaaaat agcgagaggc    60
ttttgc                                                              66

<210> SEQ ID NO 25
<211> LENGTH: 58
<212> TYPE: DNA
<213> ORGANISM: Artificial Sequence
<220> FEATURE:
<223> OTHER INFORMATION: Primer 1 for pBR322 plasmid

<400> SEQUENCE: 25
cggaatcttg cacgccctat gatcggcctg tcgcttgcat ggcctgcttc tcgccgaa     58

<210> SEQ ID NO 26
<211> LENGTH: 56
<212> TYPE: DNA
<213> ORGANISM: Artificial Sequence
<220> FEATURE:
<223> OTHER INFORMATION: Primer 2 for pBR322 plasmid

<400> SEQUENCE: 26
ggtggcggga ccagtgagcg ctctgggtca ttttcgcgaa cgccagcaag acgtag       56
```

HIGH SPEED NUCLEIC ACID MELTING ANALYSIS

This application claims priority to U.S. Provisional Patent Application Ser. No. 62/368,435, filed on Jul. 29, 2016; U.S. Provisional Patent Application Ser. No. 62/503,550, filed on May 9, 2017; and U.S. Provisional Patent Application Ser. No. 62/530,481, filed on Jul. 10, 2017, which are incorporated herein by reference in their entireties.

The present application includes a Sequence Listing filed in electronic format. The Sequence Listing is entitled "3400-319US ST25.txt" created on Nov. 3, 2017, and is 7,000 bytes in size. The information in the electronic format of the Sequence Listing is part of the present application and is incorporated herein by reference in its entirety.

BACKGROUND OF THE INVENTION

Field of the Invention

The invention relates to high speed DNA melting analysis for polymerase chain reaction (PCR) products. The melting analysis is performed in a microfluidic device allowing for precise and rapid temperature control during DNA melting.

Discussion of the Background

Microfluidics enables rapid sample processing and precise control of fluids allowing for faster turnaround time and less expensive cellular and molecular assays. For example, rare circulating tumor cells can be enriched, manipulated, and assayed in microfluidic devices.

DNA is double-stranded at room temperature, but splits apart into single-strands as the temperature is raised. By adding a fluorescent dye that fluoresces only when DNA is double-stranded, the melting of DNA, also referred to as DNA dissociation or denaturing, can be watched as the temperature is increased in real-time. High resolution DNA melting analysis, a popular method for PCR product genotyping, variant scanning, sequence identity, methylation, and copy number analysis, is currently incorporated into almost all commercial real time PCR instruments. The GC content, distribution, and sequence determines a DNA melting profile that can be used for genotyping single bases and scanning for sequence variants. A DNA melting profile is a curve representing fluorescence F as a function of sample temperature T or a curve representing a negative derivative of a fluorescence curve, $-d(F)/dT$, as a function of temperature T.

Throughput of a microfluidic device can be increased by increasing the number of parallel reactions, such as in massively parallel sequencing or digital PCR. Throughput can also be increased by shortening the turnaround time, and speed is particularly important in point of-care diagnostics. Previously, instruments required hours to melt (denature) DNA accurately for genotyping and other applications. DNA melting analysis has historically been performed at the rate of 0.01° C./s or less, requiring hours to collect a melting curve. Later, fluorescent melting analysis was introduced as a way to analyze PCR products at much faster speeds, but still less than 1° C./s. Current real-time PCR instruments that claim high resolution melting vary in the melting rates recommended. Rates from 0.005° C./s to about 0.1° C./s appear standard on currently available instruments, requiring from 5-95 min to acquire a melting curve (Li et al., "Genotyping accuracy of high-resolution DNA melting instruments," Clin Chem 2014; 60:864-72). Recent attempts to speed up nucleic acid melting analysis resulted in PCR and high speed melting being completed in a total of 12.5 min, wherein melting was performed at 0.5° C./s. (Sundberg et al., Clin Chem. 2014 October; 60(10):1306-13)).

Faster melting rates have been previously performed for some applications. Allele-specific probes annealed to microbeads monolayered on a heater allowed genotyping at 1° C./s (Russom et al., "Rapid Melting Curve Analysis on Monolayered Beads for High-Throughput Genotyping of Single-Nucleotide Polymorphisms," Anal. Chem., 2006, 78 (7), pp 2220-2225). Genotyping in less than 7 s has been reported with molecular beacons annealed to artificial templates (Ahberg et al., "Single fluorescence channel-based multiplex detection of avian influenza virus by quantitative PCR with intercalating dye," Sci Rep 2015; 5:11479). However, none of these studies are high resolution or investigate heteroduplex detection critical for genotyping used in high resolution thermal melting.

Accordingly, there is a need for a method and system to perform DNA melting analysis in seconds rather than several minutes to hours, thereby obtaining accurate melting curves sufficient for genotyping. This rapid ability to interrogate DNA should be useful whenever time to result is important, such as in molecular point of care testing. Furthermore, there is a need for determining the effect of melting rate on genotyping.

SUMMARY OF THE INVENTION

In one aspect of the invention, a method and system for performing a nucleic acid high speed melting analysis are provided. Specifically, one or more nucleic acid samples are introduced into a microfluidic device. The one or more nucleic acid samples are in optical communication with an imaging system and in thermal communication with a thermal system. The temperature of the one or more nucleic acid samples is increased by the thermal system at the ramp rate selected from a range of 1° C./s to 50° C./s to achieve nucleic acid dissociation. Images of the one or more nucleic acid samples are acquired during the nucleic acid melting (dissociation) to generate a melting (dissociation) profile. Finally, the nucleic acids are genotyped based on the melting profiles.

In one embodiment, the microfluidic device comprises a microfluidic cartridge and a reaction chip. In yet another embodiment, the reaction chip comprises one or more microchannels. In a further embodiment of the current invention, the melting analysis is performed when the one or more samples are in the one or more microchannels of the reaction chip.

According to another embodiment of the current invention, the nucleic acid melting analysis is preceded by amplification of the one or more nucleic acids. In some embodiments, the nucleic acid melting analysis is performed by increasing the temperature of the one or more nucleic acid samples at the rate selected from the range of 1° C./s to 8° C./s or from 8° C./s to 16° C./s.

In yet another embodiment, the microfluidic device is primed prior to performing the nucleic acid melting analysis. In a further embodiment, each of the one or more nucleic acid samples includes at least one internal temperature control sequence having a melting temperature that is substantially greater than a melting temperature of the nucleic acid.

In one embodiment, genotypes were classified by using a ratio of inter-class and intra-class distance thresholds for the melting rate being used. Specifically, melting curves were sequentially obtained for the one or more nucleic acid samples at a plurality of ramp rates between 0.13° C./s and 32° C./s to determine an optimal ramp rate. The optimal ramp rate corresponds to the highest genotype discrimination value, the genotype discrimination being calculated for each of the plurality of ramp rates between 0.13° C./s and 32° C./s. The ramp rate used maximizes the ratio of inter-class to intra-class distance, which minimizes the number of no-call samples and the number of false positive and false negative samples among those called. In one embodiment, a heterozygote genotype discrimination value of greater than 5 is obtained. In yet another embodiment, a heterozygote genotype discrimination value of greater than 6 is obtained.

In yet another aspect of the invention, a method for performing a nucleic acid high speed melting analysis is provided. Specifically, one or more nucleic acid samples are introduced into a microfluidic device. The one or more nucleic acid samples are in optical communication with an imaging system and in thermal communication with a thermal system. The thermal system ramps the temperature of the one or more nucleic samples to achieve nucleic acid melting (denaturing). Next, a plurality of melting curves for the one or more nucleic acid samples is sequentially obtained at a plurality of melting rates. A genotype discrimination is calculated for the plurality of melting curves for each melting rate as a ratio of inter-class to intra-class distance. The inter-class distance reflects differences between melting curves having different genotypes and the intra-class distance reflects differences between melting curves of the same genotype. Finally, an optimal melting rate that maximizes the genotype discrimination is identified.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated herein and form part of the specification, illustrate various embodiments of the subject matter of this disclosure. In the drawings, like reference numbers indicate identical or functionally similar elements.

FIG. 19A-B demonstrates genotype discrimination as a function of accelerating and decelerating melting rates for heterozygous (panel A) and homozygous (panel B).

FIG. 20A demonstrates the melting temperature (Tm) of the wild type genotype as a function of melting rate for each of the MTHFR 665, Factor 2, Factor 5, and MTHFR 1286.

FIG. 20B demonstrates the difference between each Tm in FIG. 20A and the Tm at 1° C./s as a function of melting rate for each of the of the MTHFR 665, Factor 2, Factor 5, and MTHFR 1286.

FIG. 21 is a table entitled Table 4: Blinded Study PCR Conditions.

FIG. 22 is a table entitled Table 5: Blind Test Result.

DETAILED DESCRIPTION OF THE INVENTION

The present invention has several embodiments and relies on patents, patent applications, and other references for details known in the art. Therefore, when a patent, patent application, or other reference is cited or repeated herein, it should be understood that it is incorporated by reference in its entirety for all purposes as well as for the proposition that is recited.

Using a microfluidic platform for serial PCR and melting analysis, four targets (MTHFR 665, Factor 2, Factor 5, and MTHFR 1286), each containing single nucleotide variant, were amplified and then melted at different rates over a range from 0.13 to 32° C./s. Factor 2 gene (also known as F2, FII, Factor II, F2 c.*97, F2 c.*97G>A, rs1799963)

provides instructions for making a protein called prothrombin (also called coagulation factor II). Coagulation factors are a group of related proteins that are essential for normal blood clotting. Mutations in human Factor 5 gene (also known as F5, FV, Factor V, F5 c.1601, F5 c.*1601G>A, rs6025) cause an increase in blood clotting (hypercoagulability). MTHFR 665 (also known as MTHFR c.665C>T, MTHFR c.677C>T, rs1801133) and MTHFR 1286 (also known as MTHFR c.1286A>C, MTHFR c.1298A>C, rs1801131) gene provides instructions for making the MTHFR enzyme. In other words, it "triggers" production of the enzyme. A mutation in the MTHFR gene may therefore affect enzyme function.

In one embodiment, genotypes were determined manually by visual inspection after background removal, normalization, and conversion to negative derivative plots. In yet another embodiment, automated genotyping was used. Differences between genotypes were quantified by a genotype discrimination ratio, based on inter- and intra-genotype differences using the absolute value of the maximum vertical difference between curves as a metric. Different homozygous curves were genotyped by melting temperature and heterozygous curves were identified by shape.

Figures 1A, 1B:
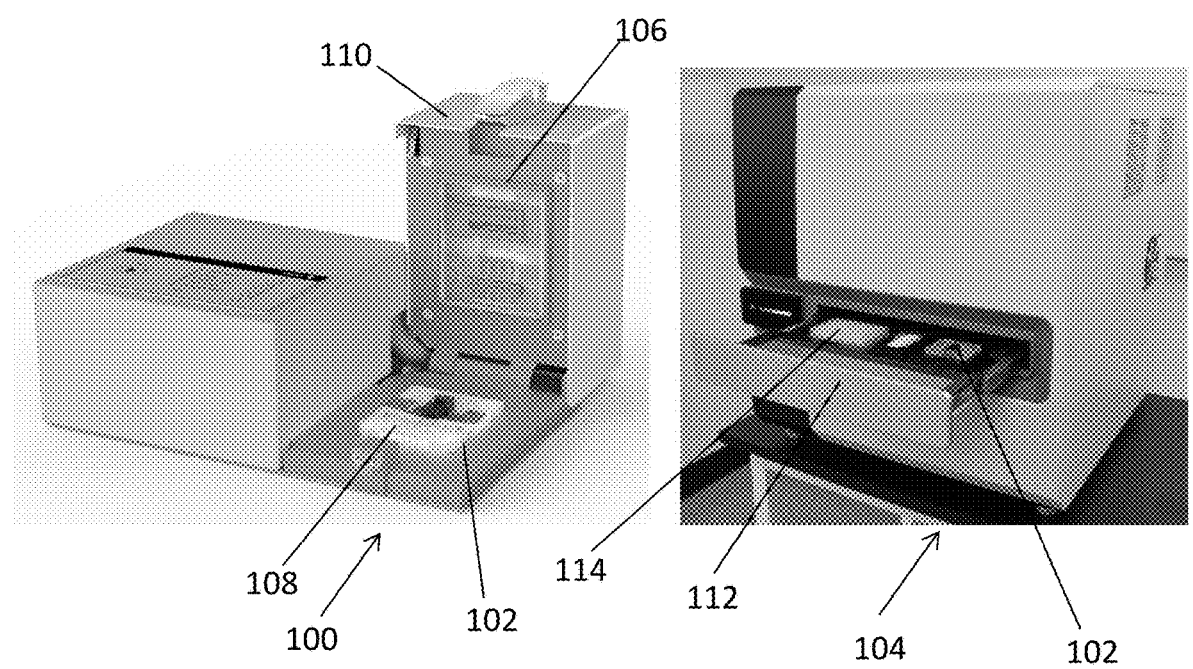
FIG. 1A-B demonstrate a priming station (A) and an instrument (B) according to the present invention used to perform high speed melting.

FIGS. 1A-B demonstrate a priming station 100 and instrument 104 used to perform high speed melting. The priming station 100 of FIG. 1A comprises interfacing gaskets 106 and a microfluidic cartridge 102 inserted therein. A microfluidic cartridge according to one embodiment of the invention is demonstrated in FIG. 2. The cartridge (interface chip) 102 may include one or more access tubes (e.g., capillary tubes or other tubes) or wells 206 connected to one or more microfluidic channels 108, 208 and waste wells 212. A reaction chip 204 may carry out reaction chemistry, such as polymerase chain reaction (PCR) amplification and thermal melting. The reaction chip 204 may include one or more microfluidic channels 210 in thermal communication with heaters 220 providing the thermal zone 218.

In one embodiment, the priming station of FIG. 1A has dimensions (31 cm×18 cm×10 cm). The priming station 100 of FIG. 1A provides a simple user workflow to ready cartridges 102 for the instrument (genetic analyzer system) 104 of FIG. 1B. The priming station's main components included valves, gaskets, and a vacuum pump (not shown). In one non-limiting embodiment, during the priming process, the microfluidic channels 108, 208 (FIG. 2) of the cartridge 102 were filled with degassed deionized water. Specifically, deionized water was loaded into the cartridge wells 206 (FIG. 2) containing capillary tube sippers, and the cartridge 102 was placed in the priming station 100. The priming station was powered on, and the lid 110 closed and latched. Once the lid 110 was closed, the gaskets 106 formed seals over the sipper, vent, and waste wells of the cartridge 102. The priming station initialized the vacuum pump and confirmed the presence of a cartridge 102. Deionized water was pipetted into a reservoir when indicated by the priming station. When the "Run" button was pressed to prime the cartridge 102, the vacuum pump applied a negative pressure over the sipper wells 206 (FIG. 2) to degas the deionized water. After several minutes, the water was pulled from the sipper wells 206 (FIG. 2) to the vent and waste wells 214 and 212 (FIG. 2) using differential pressures, filling the microchannels 210 of the reaction chip 204 (FIG. 2) with water. When priming is complete, the lid 106 is opened and the cartridge 102 removed from the priming station 100. The water is removed manually from the sipper wells 206 (FIG. 2) of the cartridge 102 to complete the priming process. In one embodiment, the priming process took about 10 min.

The priming station according to one embodiment of the invention is described in details in U.S. patent application Ser. No. 15/644,986 to Mull, filed on Jul. 10, 2017, which is incorporated by reference herein.

The instrument (genetic analyzer) 104 of FIG. 1B comprises a consumables drawer 112 open and consumables inserted. Consumables include the cartridge 102 and a 384-well microtiter plate 114 positioned within the drawer. In one embodiment, the instrument 104 has dimensions (79 cm×79 cm×79 cm). Fluid motion in the cartridge's reaction chip microchannels was monitored optically by detecting the fluorescent edge of a tracking solution that was controlled with peristaltic pumps. However, heterozygous genotyping was compromised by the small volume channel geometry, resulting in uneven distribution of wild-type and mutant DNA strands due to low copy numbers, leading to one allele being amplified more than the other within the region of fluorescence monitoring. To correct this, the tracking solution edges were shifted back and forth during PCR over a distance of about 0.9 mm, holding the edges for 20 s between each movement. This ensured that the sample's alleles were mixed well during PCR. For the final two PCR cycles, the back and forth motion ceased and the normal edge control was resumed.

Both the PCR and tracking solution robots (not shown) were provided in the instrument 104 to function simultaneously. In one embodiment, the PCR liquid handling robot was a fluid-filled system performing on board, automated mixing. A deionized water reservoir, syringe, and 9-way valve were used to flow water through the eight-channel PCR robot pipetting system. Specifically, deionized water was pumped through all eight fluidic lines (by way of example and without limitation, 900 μL) prior to starting each run. The PCR robot automatically aspirated template mixture (by way of example and without limitation 2 μL) and primer mixture (by way of example and without limitation, 1 μL) from a 384-well microtiter plate 114. The two components were mixed together by creating a bead (by way of example and without limitation, 3 μL) at the end of the pipette tip, then aspirating the bead back into the pipette tip, and repeating this process a total of eight times prior to delivering the reagent to the cartridge sippers 206 (FIG. 2) for PCR and HSM analysis.

Heating uniformity of the 8-channel microfluidic cartridge was achieved by the addition of two microfluidic heaters outside of channels 1 and 8. The additional embedded heaters reduced the temperature gradient across the outer channels for more accurate HSM. The additional embedded heaters were described in detail in the U.S. Patent Application Publication No. 2015/0069045 to Coursey et al., which is incorporated by reference herein.

In one non-limiting embodiment, the instrument 104 and the cartridge 102, described in the U.S. Patent Application Publications No. 2014/0272927, No. 2012/0058519, and No. 2009/0060795 incorporated herein by reference, were used for measuring nucleic acid melting curves.

In one non-limiting embodiment, instrument software was coded in the general purpose programming language C++, running on a real-time embedded Linux-based instrument. C++ can be used to write device drivers and other software that rely on direct manipulation of hardware under real time constraints. The instrument software controls each of the hardware components, such as heaters, robotics, pumps and optics. It also manages a user defined test workflow to perform and collect data from PCR and HSM and effectively handles any errors during a test run. The graphical user interface is a Windows-based application, written in C# and the extensible application markup language (XAML) using Windows Presentation Foundation, a next generation presentation system for building Windows client applications to provide an enhanced user experience. The graphical user interface was installed on a Windows PC and used to communicate with the instrument over transmission control protocol and Internet protocol (TCP/IP) to execute workflow and monitor status.

Figure 2:
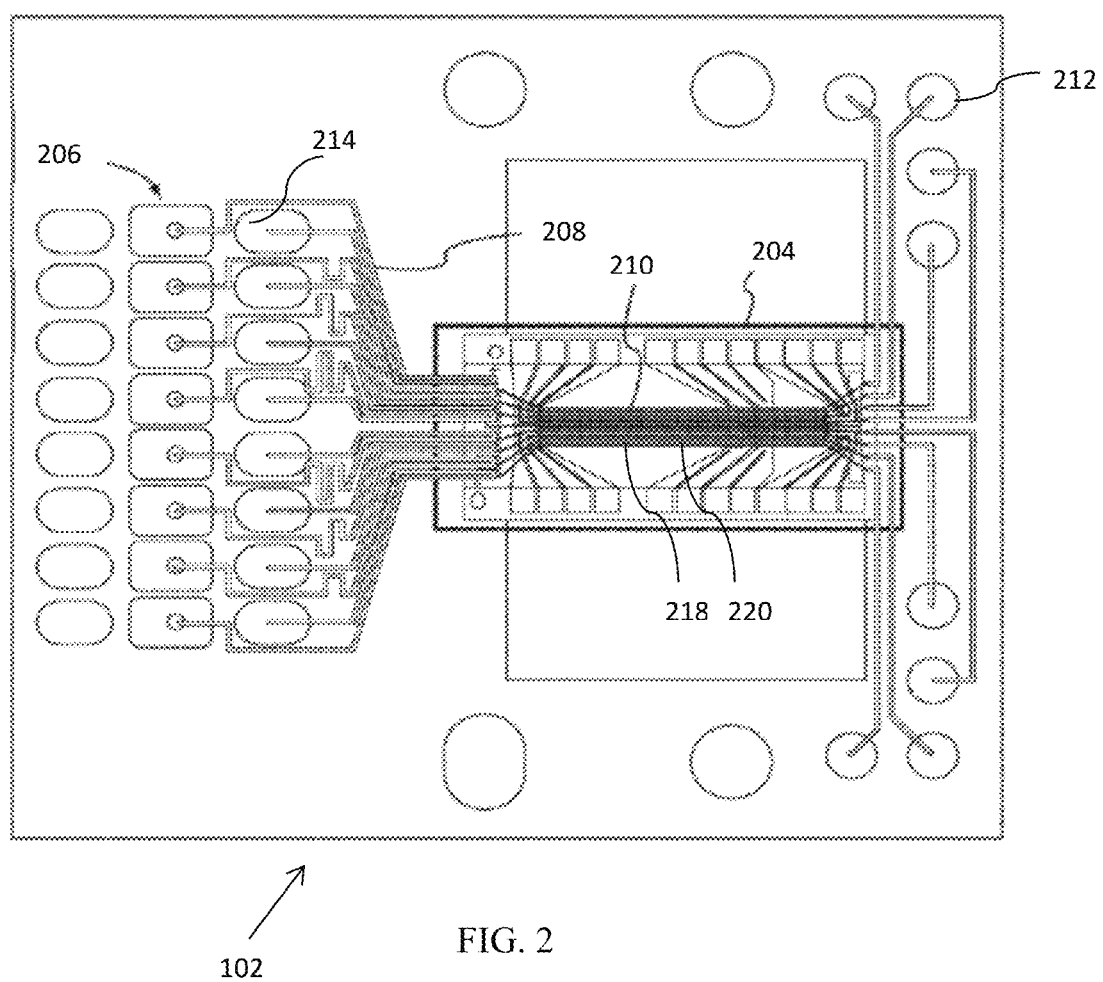
FIG. 2 illustrates a microfluidic cartridge according to one embodiment of the invention.
Figure 3:
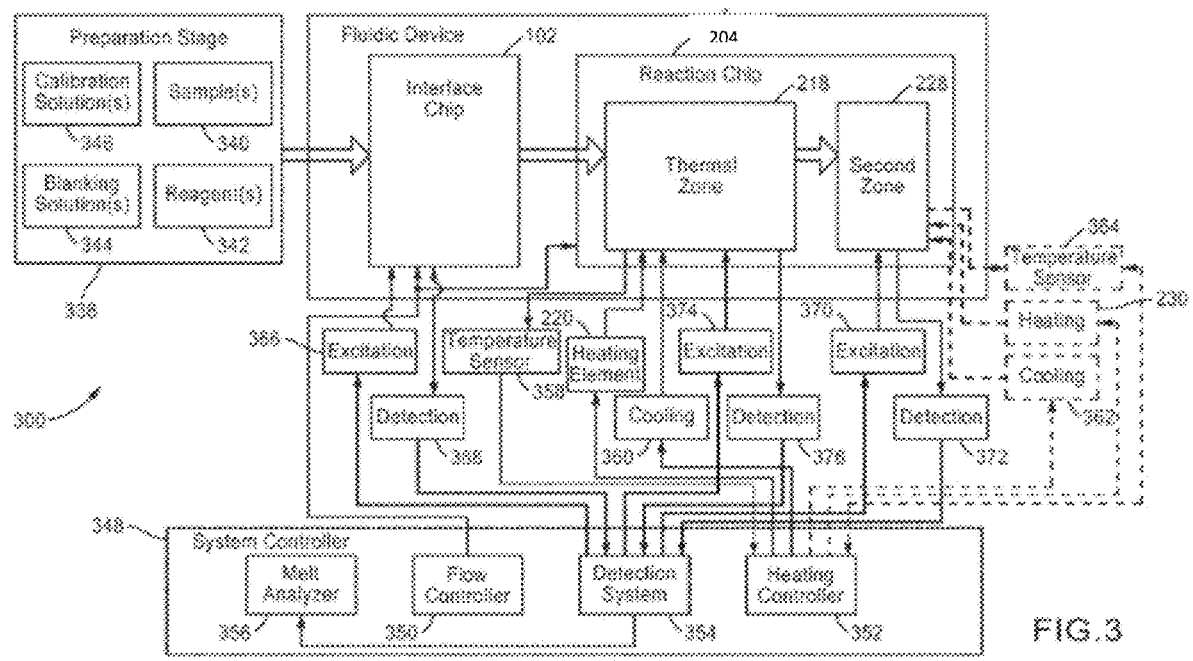
FIG. 3 illustrates a functional block diagram of a microfluidic reaction system for using a microfluidic chip, in accordance with one embodiment.
Figure 4:
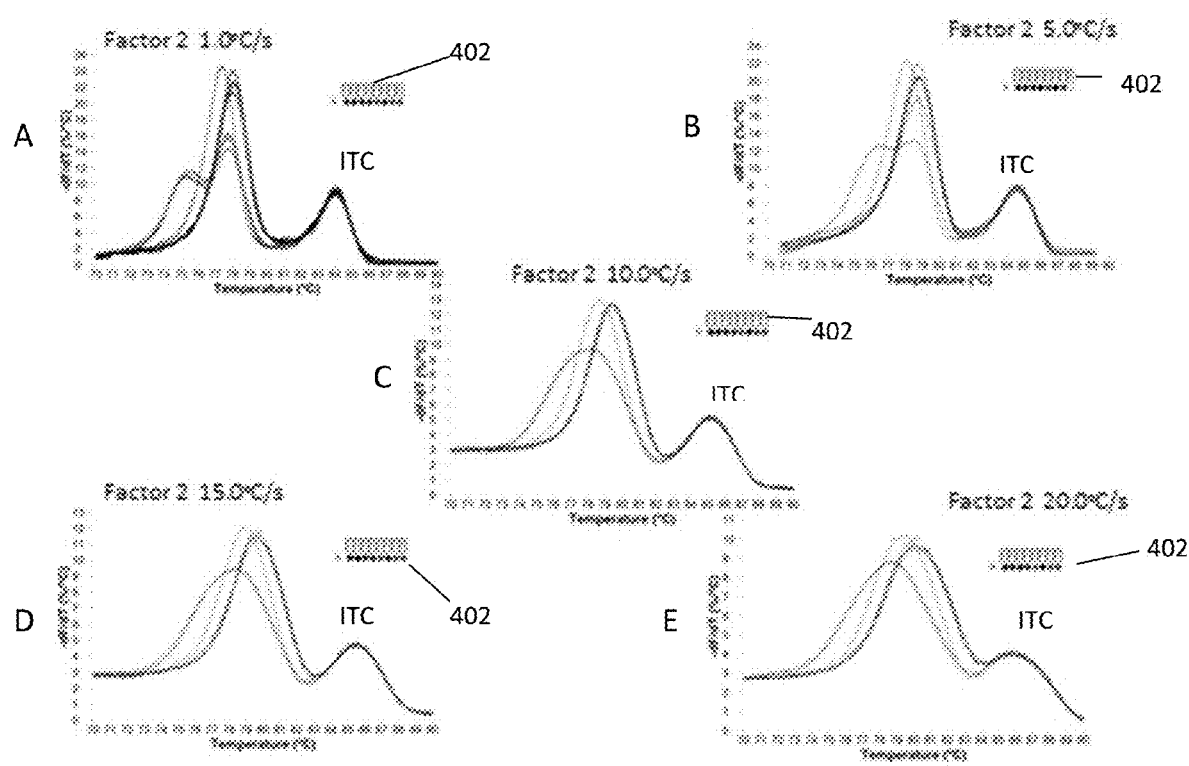
FIGS. 4A-E demonstrate negative derivatives of melting curves for Factor 2 DNA samples melted by continuously increasing the sample temperature at the rate (ramp rate) of 1° C./s, 5° C./s, 10° C./s, 15° C./s, and 20° C./s, respectively.
Figure 5:
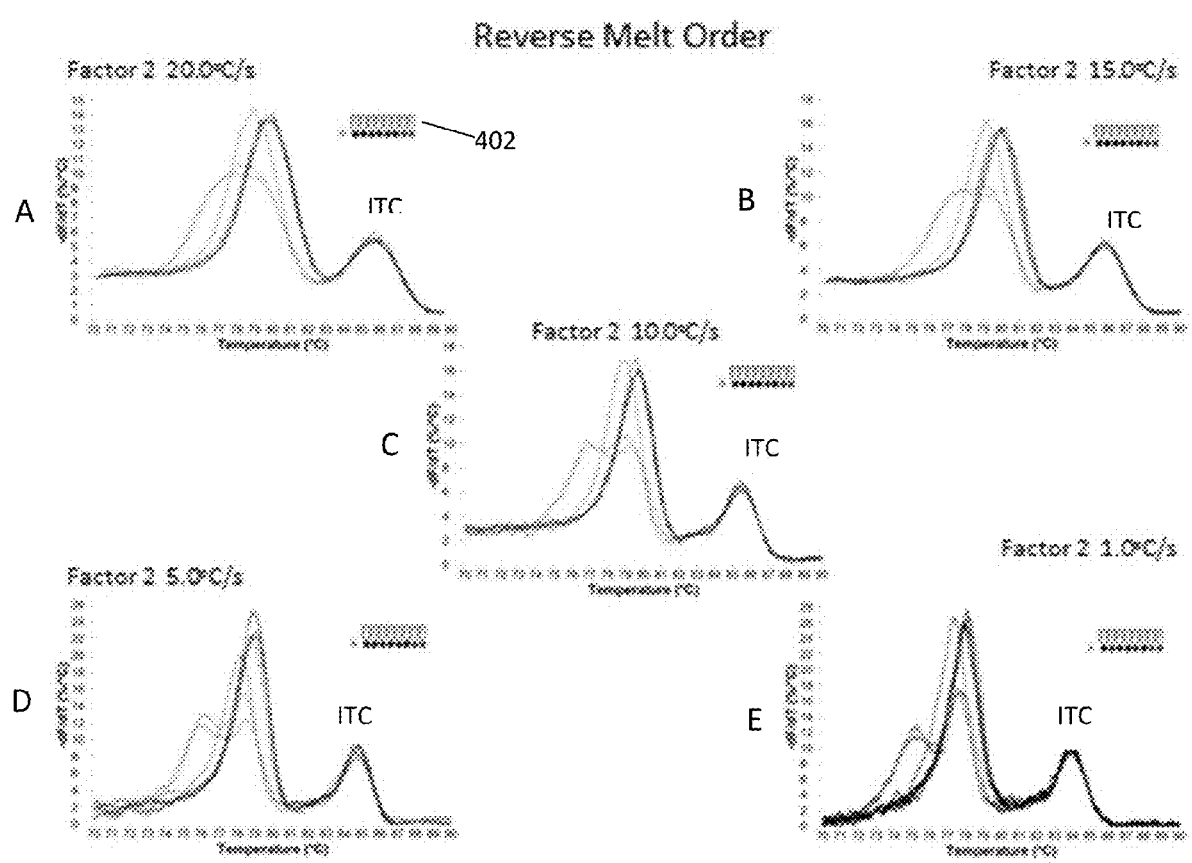
FIGS. 5A-E demonstrate melting curves for Factor 2 DNA melted by continuously increasing the sample temperature at the rate of 20° C./s, 15° C./s, 10° C./s, 5° C./s, and 1° C./s, respectively.
Figure 6:
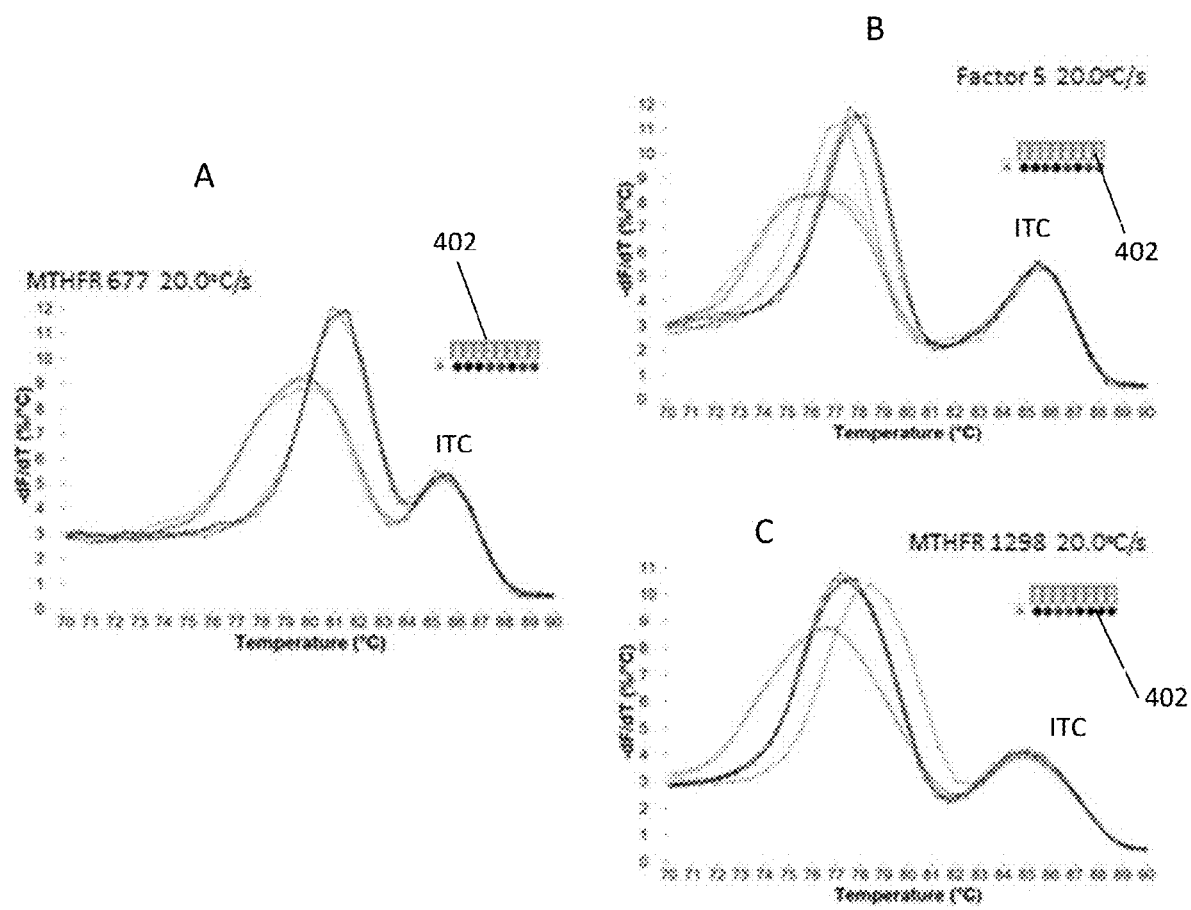
FIGS. 6A-C demonstrate melting curves for Factor 5, MTHFR 677, and MTHFR 1298 DNA melted by continuously increasing the sample temperature at the rate of 20° C./s.
Figure 7:
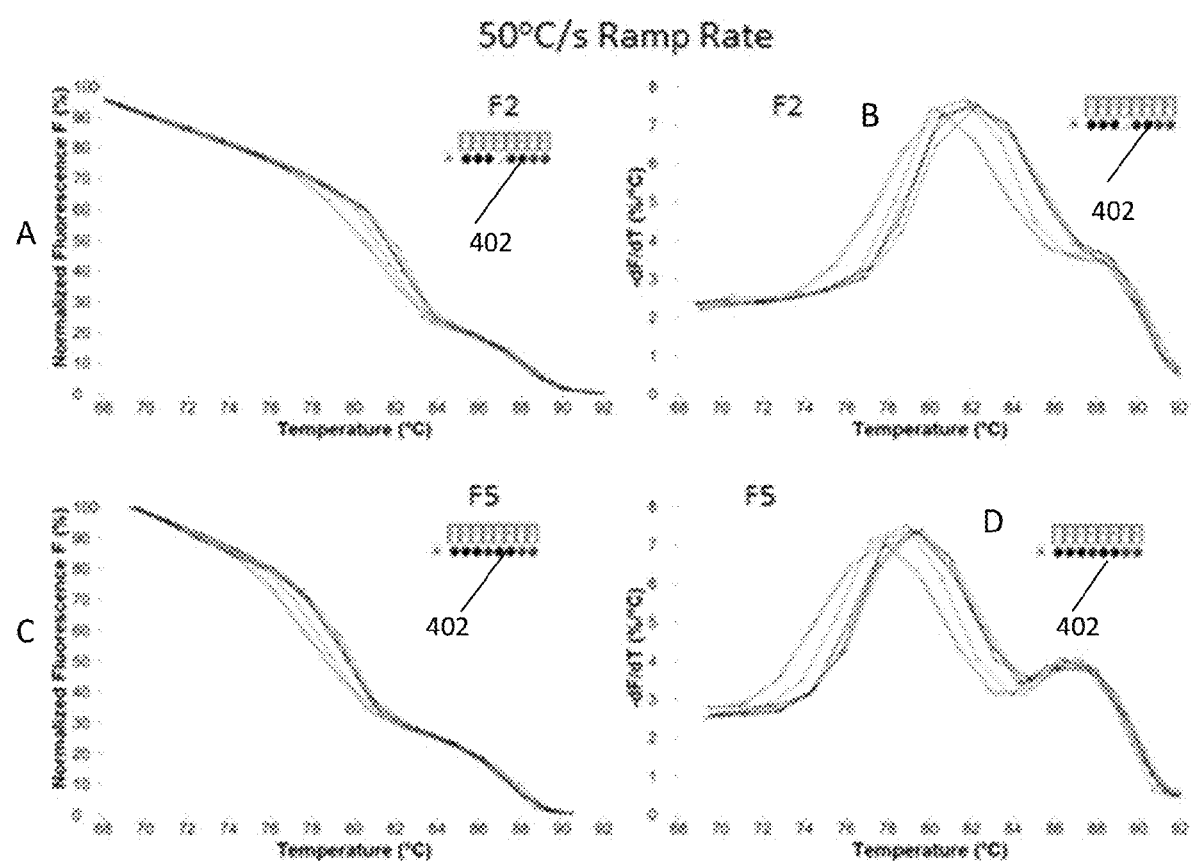
FIGS. 7A-D demonstrate melting curves for Factor 2 and Factor 5 DNA melted by continuously increasing sample temperature at the rate of 50° C./s.

FIG. 3 is a functional block diagram of a microfluidic system, in accordance with one embodiment of the present invention. In some embodiments, the microfluidic system 300 may include a preparation stage 338 (e.g., a pipettor system). In one non-limiting embodiment, the preparation stage 338 may comprise appropriate devices (e.g., PCR robots) for preparing one or more sample solutions and appropriate devices (e.g., blanking robots) for preparing one or more blanking solutions 344. For instance, as illustrated in FIG. 2, the preparation stage 338 may include one or more samples 340 and one or more reagents 342 and may prepare a sample solution by mixing a sample 340 with one or more reagents 342. The fluids input by the preparation stage 338 may also include one or more calibration solution 346. A calibration solution 346 may include a known sample having a known melting temperature. In some embodiments, fluids from the preparation stage 338 may enter into the microfluidic channels of the cartridge 102 via the access tubes or wells 206 of the cartridge 102. The fluids from the microfluidic channels of the cartridge 102 may enter the microfluidic channels of the reaction chip 204 via ports of the reaction chip 204. In the thermal zone 218 of the reaction chip 204, fluids in the microfluidic channels of the reaction chip 104 may be subjected to thermal cycling (i.e., temperature cycling) for PCR followed by a thermal ramp (i.e., temperature ramp) for melt data acquisition.

In some embodiments, the microfluidic reaction system 200 may include a system controller 348. The system controller 348 may include a flow controller 350, heating controller 352, detection system 354, and/or melt analyzer 356. The flow controller 350 may control flow of fluids through the microfluidic channels of the cartridge 102 and the microfluidic channels of reaction chip 204.

The heating controller 352 (i.e., thermal controller) may control heating of one or more heating elements 220 associated with the thermal zone. In non-limiting embodiments, control of the heating elements 220 may be based on temperatures determined by one or more temperature sensors 358 (such as, for example, RID or thin-film thermistors or thin-film thermo-couple thermometers). In this way, the temperatures of one or more channels in the thermal zone 218 may be maintained at a desired temperature, cycled through desired temperatures, and/or ramped according to one or more temperature sequences or profiles. However, in some embodiments, such as where the heating elements 220 are thin film heaters, the heating elements 220 may provide the function of the temperature sensors 358. In some embodiments of the present invention, the thermal zone 218 may also be cooled by one or more cooling devices 360, which may also be controlled by the heating controller 352. In one embodiment, a cooling device 360 could be a Peltier device, heat sink, or forced convection air cooled device, for example.

The detection system 354 may monitor flow in the channels of cartridge 102, monitor flow in the channels of reaction chip 204, and/or measure fluorescence from the reaction chip 204 during PCR amplification and/or melt data acquisition. In some embodiments where the detection system 354 monitors flow in the channels of the cartridge 102 and/or the channels of reaction chip 204, the detection system 354 may provide feedback to the flow controller 350.

In some non-limiting embodiments, the heating controller 352 (i.e., thermal controller) may have the capability to control the temperature in the second zone 228. In these embodiments, the microfluidic reaction system 300 may include one or more heating elements 230, one or more cooling elements 362, and one or more temperature sensors 364 to raise, lower, and detect the temperature of one or more channels 110 in the second zone 228, respectively. However, this is not necessary, and, in some embodiments, the microfluidic reaction system 300 may not have a heating element 230, cooling element 362, or temperature sensors 364 associated with the second zone 228. Also, as noted above, even in some embodiments where the heating controller 352 may have the capability to control the temperature in the second zone 228, the heating controller 352 may not control the heating element 230 to heat to the channels 110 in the second zone 228.

In some non-limiting embodiments, as illustrated in FIG. 3, the detection system 354 may control an interface excitation device 366 to excite a fluorescent dye (e.g., Alexa647) in fluid (e.g., blanking solution) in the channels of the cartridge 102 and receive a signal indicative of fluorescent light emitted from the fluid in the channels of the cartridge 102 and detected by a cartridge detection device 368. Similarly, the detection system 354 may control a reaction flow excitation device 370 to excite a fluorescent dye in the fluid of one or more channels in the second zone 228 of the reaction chip 204 and receive a signal indicative of fluorescent light emitted from the fluid in the one or more channels in the second zone 228 of the reaction chip 204 and detected by reaction flow detection device 372.

In some embodiments where the detection system 354 measures fluorescence of the reaction chip 204 during PCR amplification and/or melt data acquisition, the detection system 354 may control a thermal zone 218 excitation device 374 to excite a fluorescent dye in fluid in one or more channels in the thermal zone 218 of the reaction chip 204 and receive a signal indicative of fluorescent light emitted from the fluid in the one or more channels in the thermal zone 218 of the reaction chip 204 and detected by thermal zone 218 detection device 376. In some non-limiting embodiments, the thermal zone 218 excitation device may include one or more light emitting diodes (LEDs) (e.g., blue LEDs). Further, in one embodiment, the thermal zone 218 excitation device 374 may be capable of being operated in one or more modes (e.g., a low power/intensity mode and a high power/intensity mode).

In some embodiments, the system 300 may include a melt analyzer 356 capable of performing a melt analysis to identify the melting temperature of a nucleic acid in the sample slug based on the fluorescence from the portion of the sample slug in the thermal zone 218 measured by the detection system 354 during melt data acquisition. In some embodiments, the melt analyzer 356 may be a computer having a processor and memory that is programmed to perform the melt analysis. However, in alternative embodiments, the melt analyzer 356 may be an application specific integrated circuit or other digital and/or analog control circuit that is configured to perform the melt analysis.

Figure 8:
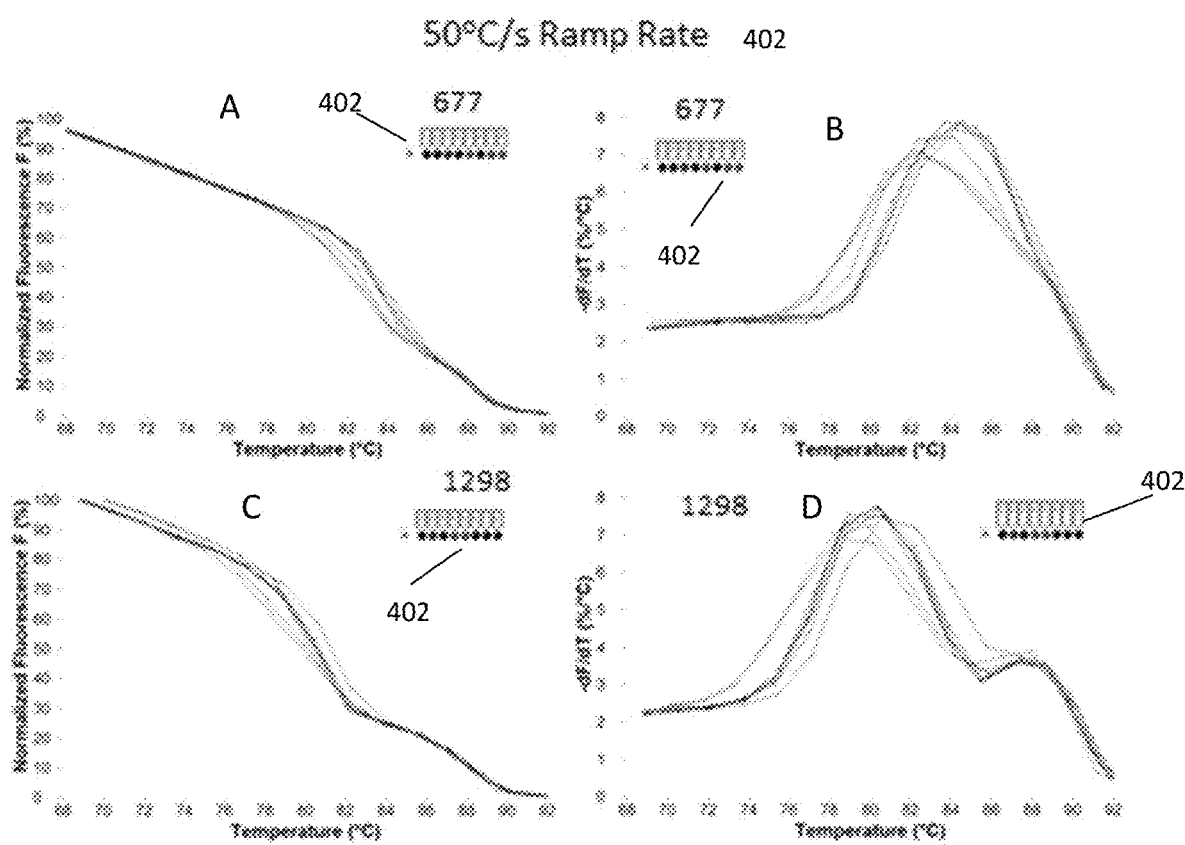
FIGS. 8A-D demonstrate melting curves for MTHFR 677 and MTHFR 1298 DNA melted by continuously increasing the sample temperature at the rate of 50° C./s.
Figure 13:
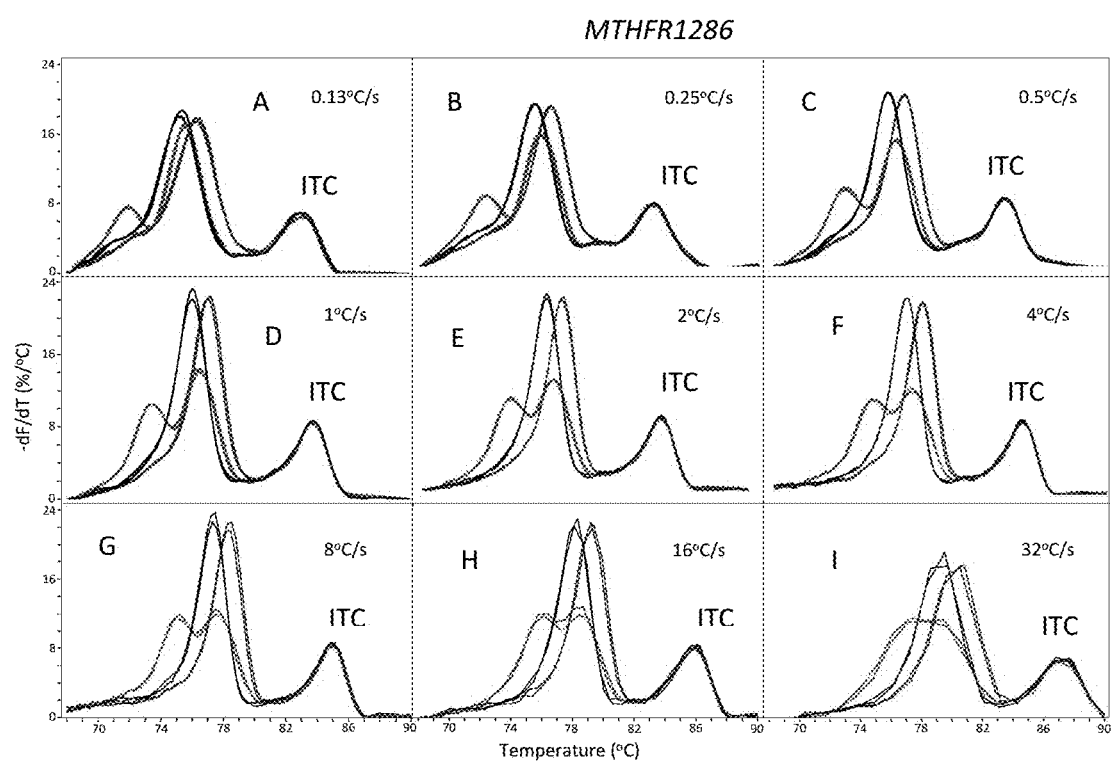
FIG. 13 A-I demonstrates the effect of melting rate on melting curves of a 46 bp PCR product encompassing the MTHFR 1286 single nucleotide variant.
Figure 14:
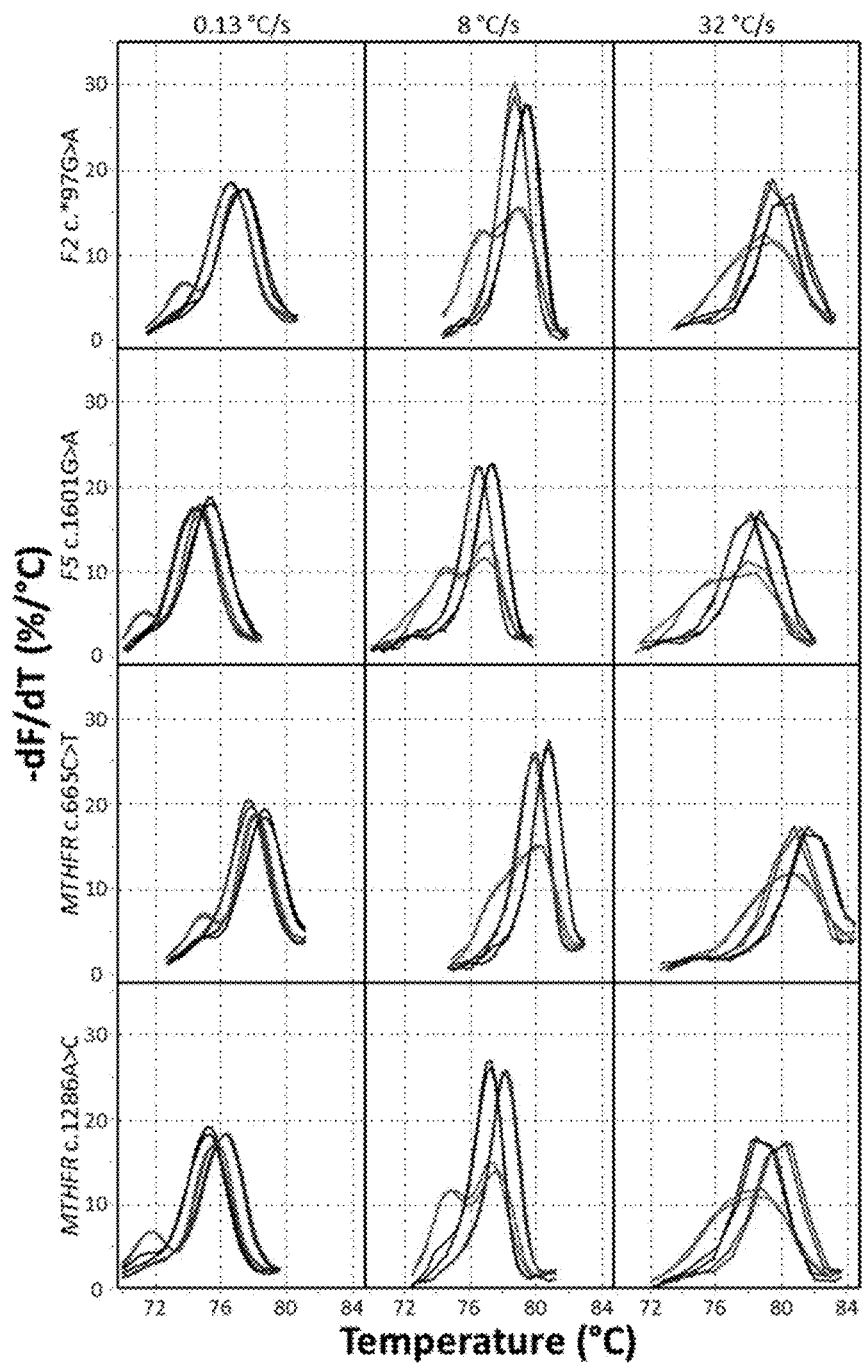
FIG. 14 demonstrates melting curves of 4 single nucleotide variants (Factor 2, Factor 5, MTHFR 665, MTHFR 1286) studied at 0.13° C./s, 8° C./s, and 32° C./s melting rates.

Curves in FIGS. 4-6, FIGS. 7B and D, FIGS. 8B and D and FIGS. 13-14 represent a negative derivative, −d(F)/dT, of a fluorescence melting curve, where T is the sample temperature and F is the fluorescence indicative of DNA denaturation. In one non-limiting embodiment, the curves in FIGS. 4-8 and FIGS. 13-14 were measured by using the instrument 104, the cartridge 102, reaction chip 204, and the system 300 as described above with reference to FIGS. 1-3. Each of the samples (MTHFR 665, Factor 2, Factor 5, and MTHFR 1286) was measured along with an internal temperature control (ITC) to control for minor temperature variation between channels.

Example 1 (Factor 2)

FIGS. 4A-F and FIGS. 5A-F relate to melting (dissociation, denaturing) analysis of Factor 2 DNA obtained in a PCR reaction. Each of FIGS. 4A-F demonstrates exemplary negative derivatives of DNA melting curves (also referred to as denaturation or dissociation curves) for different Factor 2 DNA samples melted in eight channels of the microfluidic chip (i.e. reaction chip 204 of FIG. 2). For each channel of the microfluidic chip, multiple melting reactions are performed on Factor 2 DNA samples by increasing the sample temperature at the ramp rates of 1° C./s (FIG. 4A), 5° C./s (FIG. 4B), 10° C./s (FIG. 4C), 15° C./s (FIG. 4D), and 20° C./s (FIG. 4F). Accordingly, a sample in each channel is subsequently melted at 1° C./s, 5° C./s, 10° C./s, 15° C./s, and 20° C./s rates.

As illustrated by diagram 402, each channel has a different Factor 2 DNA sample. Specifically, channels 1-3 and 6 (counting from left to right) have wild type Factor 2 DNA samples (shown in black); channel 4 has a Factor 2 DNA sample with a homozygous mutation (shown in blue); channels 5, 7, and 8 have Factor 2 DNA samples with a heterozygous mutation (shown in red). Each of FIGS. 4A-F demonstrates three types of curves, e.g. negative derivatives of melting curves corresponding to wild type Factor 2 DNA samples, negative derivative of a melting curve corresponding to Factor 2 DNA sample having a homozygous mutation, and negative derivatives of melting curves corresponding to Factor 2 DNA sample having a heterozygous mutation. The wild type and homozygous curves are similar in shape, but are distinguished by different melting temperatures. In contrast, heterozygous curves exhibit a different shape having a different number of peaks. However, the double peak heterozygous curves can be observed only at the ramp rates of 1° C./s (FIG. 4A) and 5° C./s (FIG. 4B). There is still a shape difference between wild type, homozygous, and heterozygous curves even at the faster rates (broader peak, lower peak height), but the double peak is no longer apparent at the ramp rates of 10° C./s (FIG. 4C), 15° C./s (FIG. 4D), and 20° C./s (FIG. 4F). The loss of double peak may have to do with lower data density and the data being smoothed more.

FIGS. 5A-F show negative derivatives of melting curves corresponding to the same experiment setup as shown in FIGS. 4A-F, but performed in reversed order. Specifically, a sample in each channel is subsequently melted at 20° C./s (FIG. 5A), 15° C./s (FIG. 5B), 10° C./s (FIG. 5C), 5° C./s (FIG. 5D), and 1° C./s (FIG. 5F) rates. The double peak difference in shape between wild type, homozygous, and heterozygous curves can be observed only at the ramp rates of 1° C./s (FIG. 5F), 5° C./s (FIG. 5D), and 10° C./s (FIG. 5C).

Example 2 (Factor 5, MTHFR 677, and MTHFR 1298)

FIGS. 6A-C relate to melting analysis of Factor 5, MTHFR 677, and MTHFR 1298 DNA melted by increasing the sample temperature at the rate of 20° C./s. The microfluidic chip has eight channels each of which may have one of wild type, homozygous, and heterozygous samples as indicated by diagram 402.

FIG. 6A relates to melting MTHFR 677 DNA by increasing the sample temperature at the rate of 20° C./s. Specifically, as indicated by reference number 402, channels 1-3 and 6 (counting from left to right) have a wild type MTHFR 677 DNA sample (shown in black). Channels 4, 5, 7, and 8 have MTHFR 677 DNA sample with a heterozygous mutation (shown in red).

FIG. 6B relates to melting Factor 5 DNA by increasing sample temperature at 20° C./s. Specifically, channels 1, 2, and 6 have a wild type (black curve) Factor 5 DNA. Channels 5 and 6-7 have Factor 5 DNA with a heterozygous mutation (red curve). Finally, channel 3 has Factor 5 DNA with a homozygous mutation (blue curve).

FIG. 6C relates to melting MTHFR 1298 DNA by increasing the sample temperature at 20° C./s. Specifically, channels 1 and 5-8 have a wild type MTHFR 1298 DNA (shown in black). Channels 5 and 4 have MTHFR 1298 DNA with a heterozygous mutation (shown in red). Finally, channel 2 has MTHFR 1298 DNA with a homozygous mutation (shown in blue).

Example 3 (Factor 2 and Factor 5)

FIG. 7A demonstrates melting curves representing normalized fluorescence F as a function of temperature for Factor 2 DNA samples. FIG. 7B shows a negative derivative of the normalized fluorescence, −d(F)/dT, as a function of temperature for Factor 2 DNA samples. To achieve dissociation of double strand DNA in a sample, the sample temperature increases at the rate of 50° C./s. As indicated by diagram 402, channels 1-3 and 6 of the microfluidic chip have a wild type Factor 2 DNA (black curve); channel 5 has Factor 2 DNA with a homozygous mutation (blue curve); and channels 7 and 8 have Factor 2 DNA with a heterozygous mutation (red curve).

FIG. 7C demonstrates melting curves representing normalized fluorescence F as a function of temperature for Factor 5 DNA samples. FIG. 7D shows a melting curve representing a negative derivative of the normalized fluorescence, −d(F)/dT, as a function of temperature for Factor 5 DNA samples. To achieve dissociation of double strand DNA in a sample, the sample temperature increases at the rate of 50° C./s. Channels 1-3 and 5-6 of the microfluidic chip have a wild type Factor 5 DNA (black curve); channel 4 has Factor 5 DNA with a homozygous mutation (blue curve); and channels 7 and 8 have Factor 5 DNA with a heterozygous mutation (red curve). Accordingly, even at the ramp rate of 50° C./s the samples still can be genotyped.

Example 4 (MTHFR 677 and MTHFR 1298)

FIG. 8A demonstrates normalized fluorescence F as a function of temperature for MTHFR 677 DNA samples. FIG. 8B shows a negative derivative of the normalized fluorescence, −d(F)/dT, as a function of temperature for MTHFR 677 DNA samples. To achieve dissociation of double strand DNA in a sample, the sample temperature increases at the rate of 50° C./s. Channels 1, 2, 4, and 6 of the microfluidic chip have a wild type MTHFR 677 DNA (black curve); channel 3 has MTHFR 677 DNA with a homozygous mutation (blue curve); and channels 5, 7, and 8 have MTHFR 677 DNA with a heterozygous mutation (red curve).

FIG. 8C demonstrates normalized fluorescence F as a function of temperature for MTHFR 1298 DNA samples. FIG. 8D shows a negative derivative of the normalized fluorescence, −d(F)/dT, as a function of temperature for MTHFR 1298 DNA samples. To achieve dissociation of double strand DNA in a sample, the sample temperature increases at the rate of 50° C./s. Channels 1, 3, and 6-8 of the microfluidic chip have a wild type MTHFR 1298 DNA (black curve); channel 2 has MTHFR 1298 DNA with a homozygous mutation (blue curve); and channels 4 and 5 have MTHFR 1298 DNA with a heterozygous mutation (red curve). Accordingly, even at the ramp rate of 50° C./s the samples still can be genotyped.

Figure 9:
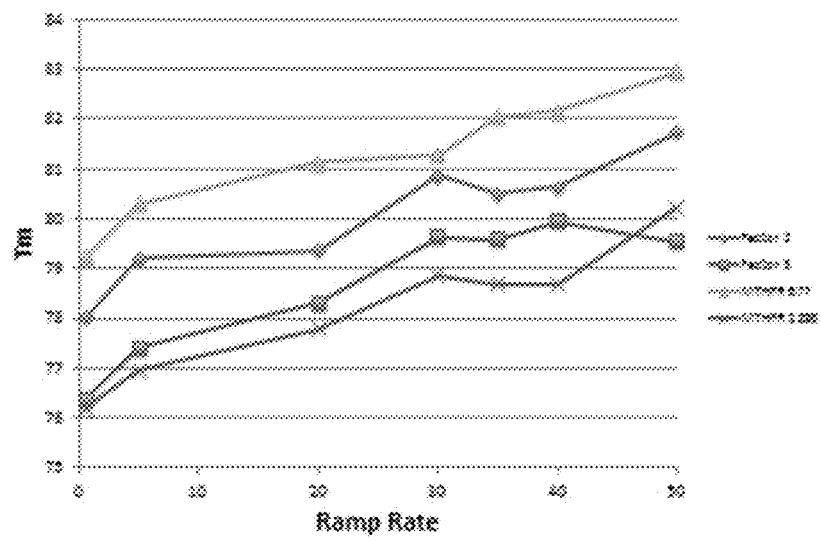
FIG. 9 demonstrates detected melting temperatures of Factor 2, Factor 5, MTHFR 677, and MTHFR 1298 wild type DNA as a function of the ramp rate, the ramp rate being in the range of 0.01° C./s to 50° C./s.
Figure 10:
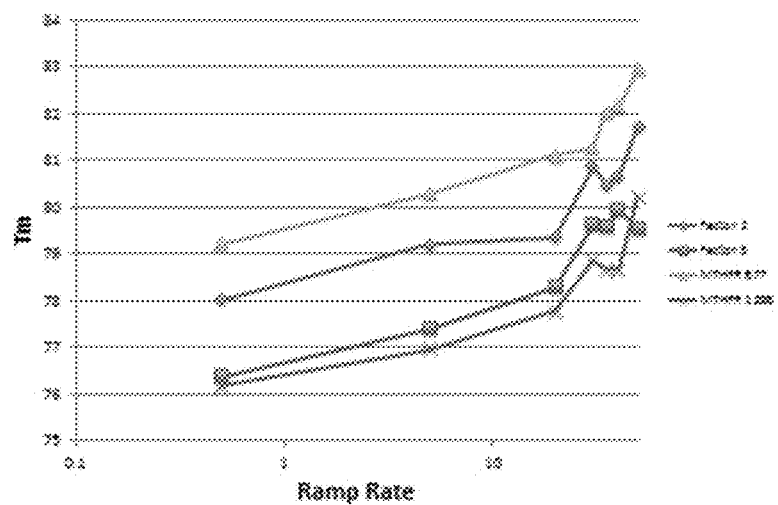
FIG. 10 demonstrates the melting temperature of Factor 2, Factor 5, MTHFR 677, and MTHFR 1298 wild type DNA on a logarithmic scale, the ramp rate being in the range of 0.01° C./s to 20° C./s.
Figures 11, 12:
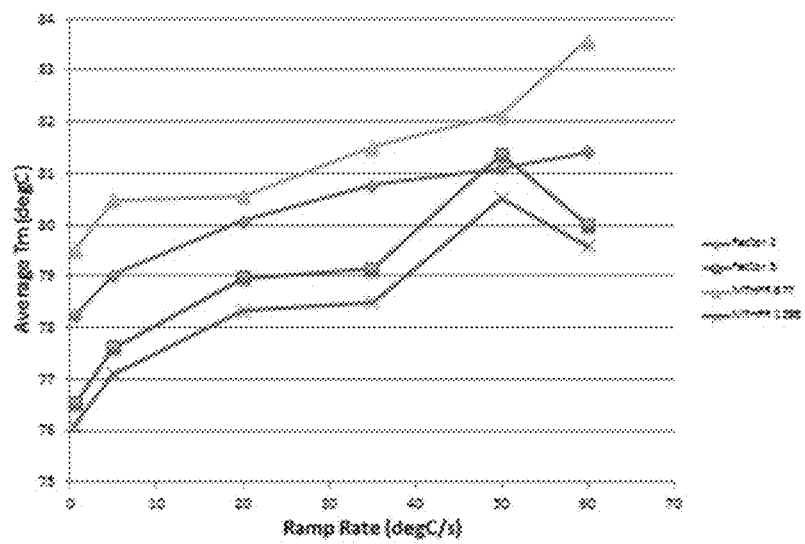
FIG. 11 demonstrates the melting temperature of Factor 2, Factor 5, MTHFR 677, and MTHFR 1298 wild type DNA as a function of the ramp rate, the ramp rate being in the range of 0.01° C./s to 60° C./s.
FIG. 12 demonstrates the melting temperature of Factor 2, Factor 5, MTHFR 677, and MTHFR 1298 wild type DNA on a logarithmic scale, the ramp rate being in the range of 0.01° C./s to 60° C./s.

FIGS. 9 and 11 demonstrate dependency of the detected DNA melting temperature from the temperature ramp rate during melting process. FIGS. 10 and 12 demonstrate dependency of the detected DNA melting temperature from the temperature ramp rate on a logarithmic scale. Specifically, the melt temperatures of wild type Factor 2, wild type Factor 5, wild type MTHFR 677, and wild type MTHFR 1298 are plotted at different temperature ramp rates. The ramp rates range from 0.01 to 50° C./s in FIG. 9 and from 0.01 to 60° C./s in FIG. 11. Accordingly, FIGS. 9-12 demonstrate that as melting rate increases the melting temperature, Tm, shifts which alludes to the fact that there is some temperature delay of actual fluid temperature versus instrument readings.

Further examples of high speed melting analysis performed at melting rates varying from 0.13 to 32° C./s with acquisition times from about 4 min to less than 1 s are provided below. Specifically, four genetic loci related to coagulation, Factor 2, Factor, MTHFR 665 and MTHFR 1286, were amplified and melted in a high speed genetic analyzer of FIG. 1B that performed rapid PCR followed by high speed melting (HSM). In one non-limiting embodiment, for each cartridge run, the melting of each PCR product was repeated nine times at different rates from 0.13 to 32° C./s, ordered either as accelerating or decelerating rates. The nine rates from eight microfluidic cartridges over four loci resulted in 288 data sets to analyze. Each eight channel data set included two wild-type, two homozygous variant, two heterozygous variant, one negative control and one genomic DNA sample. The negative control melting curves showed the internal temperature controls as expected, but were otherwise negative.

Oligonucleotides

Primers, controls, and calibrators were synthesized by standard phosphoramidite chemistry (Integrated DNA Technologies), and their sequences are shown in Table 1.

TABLE 1

Oligonucleotide sequences for primers, internal controls, and calibrators.

| Identifier | Oligonucleotide Sequence (5'-3') |
| --- | --- |
| F2 c.*97G > A Forward | GTTCCCAATAAAAGTGACTCTCAG (SEQ ID NO: 1) |
| F2 c.*97G > A Reverse | TAGCACTGGGAGCATTGAG (SEQ ID NO: 2) |
| F5 c.1601G > A Forward | GCAGATCCCTGGACAGG (SEQ ID NO: 3) |
| F5 c.1601G > A Reverse | CAAGGACAAAATACCTGTATTC (SEQ ID NO: 4) |

TABLE 1-continued

Oligonucleotide sequences for primers, internal controls, and calibrators.

| Identifier | Oligonucleotide Sequence (5'-3') |
| --- | --- |
| MTHFR c.665C > T Forward | TTGAAGGAGAAGGTGTCTGC (SEQ ID NO: 5) |
| MTHFR c.665C > T Reverse | AAGCTGCGTGATGATGAAAT (SEQ ID NO: 6) |
| MTHFR c.1286A > C Forward | GGAGGAGCTGACCAGTGAA (SEQ ID NO: 7) |
| MTHFR c.1286A > C Reverse | AAGAACGAAGACTTCAAAGACACTT (SEQ ID NO: 8) |
| Internal Temp Control Forward | TTGGGCCCCTCCGACACGAGCCCGGCTAGCC TGCATCCTGCCAGX[a] (SEQ ID NO: 9) |
| Internal Temp Control Reverse | CTGGCAGGATGCAGGCTAGCCGGGGCTCGTGT CGGAGGGGCCCAAX[a] (SEQ ID NO: 10) |
| Low $T_m$ Calibrator Forward | ATCGTGATTTCTATAGTTATCTAAGTCGTTAT ATA (SEQ ID NO: 11) |
| Low $T_m$ Calibrator Reverse | TATATAACGACTTAGATAACTATAGAAATCAC GAT (SEQ ID NO: 12) |
| High $T_m$ Calibrator Forward | TTGCGGTGGGCCACGGCGCGGCGGCAGCGCTT CGCTTCTGCGCCA (SEQ ID NO: 13) |
| High $T_m$ Calibrator Reverse | TGGCGCAGAAGCGAAGCGCTGCCGCCGCGCCG TGGCCCACCGCAA (SEQ ID NO: 14) |

[a]X is a 3'-amino modifier (see Methods).

The F2 primers yielded a 48 base pair (bp) product, F5 primers a 43 bp product, MTHFR c.665 primers a 48 bp product, and MTHFR c.1286 primers a 46 bp product. A 45 bp duplex internal temperature control was composed of 3'-phosphate terminated complementary oligonucleotides and included in all reactions. Low and high melting temperature (Tm) calibrators for temperature calibration were used as previously described (Cao et al., "Automated microfluidic platform for serial polymerase chain reaction and high-resolution melting analysis. J Lab Autom 2016; 21:402-11). Double-stranded DNA templates (gBlocks®, Integrated DNA Technologies) were synthesized for the Factor 2, Factor 5, and two MTHFR variant loci for inclusion with the appropriate primer pair specified above. Template sequences are provided in Table 2.

TABLE 2

Oligonucleotide template sequences[a]

| Identifier | Oligonucleotide Template (5'-3')[b] |
| --- | --- |
| F2.*97G > A | GTAGGGGGCCACTCATATTCTGGGCTCCTGGAACC AATCCCGTGAAAGAATTATTTTTGTGTTTCTAAAA CTATGGTTCCCAATAAAAGTGACTCTCAGC[G/A] AGCCTCAATGCTCCCAGTGCTATTCATGGGCAGCT CTCTGGGCTCAGGAAGAGCCAGTAATACTACTGGA TAAAGAAGACTTAAGAATCCACCACCTGGT (SEQ ID NO: 15) |

TABLE 2-continued

Oligonucleotide template sequences[a]

| Identifier | Oligonucleotide Template (5'-3')[b] |
|---|---|
| F5c.1601G > A | TTAACAAGACCATACTACAGTGACGTGGACATCAT GAGAGACATCGCCTCTGGGCTAATAGGACTACTTC TAATCTGTAAGAGCAGATCCCTGGACAGGC[G/A] AGGAATACAGGTATTTTGTCCTTGAAGTAACCTTT CAGAAATTCTGAGAATTTCTTCTGGCTAGAACATG TTAGGTCTCCTGGCTAAATAATGGGGCATT (SEQ ID NO: 16) |
| MTHFRc.665C > T | TGACTGTCATCCCTATTGGCAGGTTACCCCAAAGG CCACCCCGAAGCAGGGAGCTTTGAGGCTGACCTGA AGCACTTGAAGGAGAAGGTGTCTGCGGGAG[C/T] CGATTTCATCATCACGCAGCTTTTCTTTGAGGCTG ACACATTCTTCCGCTTTGTGAAGGCATGCACCGAC ATGGGCATCACTTGCCCCATCGTCCCCGG (SEQ ID NO: 17) |
| MTHFRc.1286A > C | GCCTTTGGGGAGCTGAAGGACTACTACCTCTTCTA CCTGAAGAGCAAGTCCCCCAAGGAGGAGCTGCTGA AGATGTGGGGGAGGAGCTGACCAGTGAAG[A/C] AAGTGTCTTTGAAGTCTTCGTTCTTTACCTCTCGG GAGAACCAAACCGGAATGGTCACAAAGTGAGTGAT GCTGGAGTGGGGACCCTGGTTCATCCCCTG (SEQ ID NO: 18) |

[a]Only one strand of the double-stranded template is shown.
[b]Forward primers are shown in blue, the SNVs of interest in red, and the inverse complement of the reverse primers in green.

the reverse primers in green.

In one non-limiting embodiment, both wild-type and homozygous variant templates were synthesized for each locus, and heterozygous DNA samples were obtained by mixing equal amounts of wild-type and variant synthetic templates. The synthetic templates ranged from 200 to 201 bp long. All oligonucleotides were quantified by UV absorbance at 260 nm.

Polymerase Chain Reaction

In one non-limiting embodiment, genotyping assays for F2 c.*97G>A, F5 c.1601G>A, MTHFR c.665C>T and MTHFR c.1286A>C were performed on the instrument described in FIGS. 1A, 2, and 3. A 384-well plate (i.e. 114, FIG. 1B) was first loaded with reagents manually, including a primer mixture for each assay and a template mixture for each sample analyzed. Each primer mixture included 2 primers, the 2 oligonucleotides making up the duplex internal temperature control, dNTPs, and common buffer reagents including Tris, KCl, MgCl2, betaine, DMSO and Tween®20. Each template mixture included a variant of Taq DNA polymerase with anti-Taq antibody (by way of example and without limitation, Titanium® Taq, Takara Bio USA), LCGreen® Plus dye (BioFire Defense), bovine serum albumin (BSA), the common buffer components listed above, and template DNA. The template DNA was added last to each template mixture, consisting of either a synthetic template (homozygous wild-type, homozygous mutant, or heterozygous), human genomic DNA (wild-type at each of the 4 loci), or water (for the no template control). Separating the primer mixture (primers, internal temperature control, dNTPs) from the template mixture (polymerase/antibody, BSA, dye, and template) until just before PCR was used to limit non-specific amplification.

The primer and template mixtures were combined robotically by the instrument just before amplification and analysis. The final mixed concentrations in the PCR were: 20 mM Tris, pH 8.3, 30 mM KCl, 1 M betaine, 2% DMSO, 0.05% BSA, 0.04% Tween®20, 4.5 mM MgCl2, 1.5 mM total dNTPs, 0.5 µM of the ITC, 1.0 µM each primer, 1× LCGreen® Plus dye, 1× Titanium® Taq DNA polymerase including TaqStart® antibody, and DNA template (either the synthetic template, genomic DNA or water for the no template control). When synthetic templates were used, their final concentration was 0.002 pg/µL (about 10,000 copies/µL). When genomic DNA was the template, 20 ng/µL was used (about 6,400 haploid copies/µL). These concentrations produced similar quantification cycles (Cqs) with real-time PCR for each target, suggesting that the synthetic templates may not all be full length and/or pure. In one non-limiting embodiment, the microchips (i.e. reaction chip 204 of FIG. 2) were designed to run 8 samples at a time in the following positions on each microfluidic cartridge:

Channel 1: Wild-type genomic DNA
Channel 2: Wild-type synthetic template
Channel 3: Heterozygous synthetic template
Channel 4: Homozygous mutant synthetic template
Channel 5: Heterozygous synthetic template
Channel 6: Wild-type synthetic template
Channel 7: Homozygous mutant synthetic template
Channel 8: No template control Rapid temperature cycling included heating at a programmed melting rate of 50° C./s to 95° C. with an initial denaturation hold of 30 s, followed by 40 cycles of cooling at 12.5° C./s to X° C. with a 2 s hold, heating to 72° C. at 1.8° C./s with a 3 s hold, and heating at 50° C./s to 95° C. with a 2 s hold. The annealing temperature (X° C.) varied by assay: F2: X=65° C., F5: X=62° C., MTHFR c.665: X=60° C. and MTHFR c.1286: X=62° C. The time to complete PCR was 10 min for F2, 11.3 min for F5 and MTHFR c. 1286 and 12.2 min for MTHFR c. 665. Following 40 cycles of PCR, there was an additional denature/renature step that was completed in 8 s: heating at a programmed 200° C./s to 95° C. with a 1.5 s hold, followed by cooling at a programmed 200° C./s to 50° C. for a 2 s hold.

High Speed Melting (HSM)

After PCR, the samples remained in the same microfluidic channel positions for HSM performed between 65° C. and 95° C. with a camera acquisition rate of 30 frames per second. Each product was melted 9 times, at 0.13, 0.25, 0.5, 1, 2, 4, 8, 16, and 32° C./s, either beginning with the slowest speed progressing to the fastest, or beginning at the fastest speed progressing to the slowest. Corresponding melting times and data acquisition densities are given in Table 3.

SUPPLEMENTAL TABLE 3

Correlation between the 9 ramp rates, melting time[a], and data density.

| | Ramp Rate (° C./s) | Melting Time (s) | Number of Points/° C. |
|---|---|---|---|
| a. | 0.13 | 231 | 226 |
| b. | 0.25 | 120 | 118 |
| c. | 0.5 | 60 | 59.0 |
| d. | 1 | 30 | 29.6 |
| e. | 2 | 15 | 14.8 |
| f. | 4 | 7.5 | 7.45 |
| g. | 8 | 3.75 | 3.78 |
| h. | 16 | 1.88 | 1.96 |
| i. | 32 | 0.94 | 1.10 |

[a]Time to acquire a 30° C. temperature span.

In one embodiment, eight microfluidic cartridges, as illustrated in FIG. 2, were run, four at two sites. At each site, two cartridges were run with melting fast-to-slow and two with melting slow-to-fast.

Example 5 (MTHFR 1286)

FIGS. 13A-I demonstrate the effect of melting rate on PCR product melting curves containing a single nucleotide variant. In one embodiment, a 46 bp PCR product encompassing the MTHFR c.1286A>C locus was amplified and repeatedly melted at different rates along with an internal temperature control (ITC). Melting data were processed by exponential background removal, normalization, and linear temperature adjustment to the internal temperature control to compensate for any temperature variation between channels. Negative derivative plots of melting curves at each melting rate show two wild-type samples as black lines (WT), two homozygous variants as blue lines (HOM) and two heterozygotes (HET) as red lines. The PCR product melts around 70-83° C. while the internal temperature control melts higher, around 83-87° C. Apparent melting temperatures increase with the melting rate (See FIG. 20A). The duplicate genotypes cluster distinctly and the lower temperature heteroduplex peaks increase in height to become more even with higher peak as the ramp rate increases. At 32° C./s, heteroduplex and homoduplex peaks merge into a single, broad peak because of low data density. Nevertheless, genotyping is clearly possible at all rates.

Example 6

FIG. 14 demonstrates negative derivatives of melting curves of 4 SNV loci (F2 c.*97G>A, F5 c.1601G>A, MTHFR c.665C>T and MTHFR c.1286A>C) studied at slow (0.13° C./s), fast (8° C./s), and very fast (32° C./s) melting rates. Specifically, normalized negative derivatives are displayed at three melting rates after background removal, normalization, and temperature adjustment to the internal temperature control (internal temperature control (ITC) peak is not shown). Each panel includes synthetic duplicates of the three genotypes with wild-type (black), homozygous variant (blue), and the heterozygote (red). Small heteroduplex peaks at 0.13° C./s become larger and similar in height to the homoduplex peaks at 8° C./s, while homozygous peaks become taller and narrower. At 32° C./s, heterozygous duplex peaks merge into a single broad peak as data acquisition rates limit homozygous peak sharpness, but all genotypes remain easily distinguishable.

Figure 15:
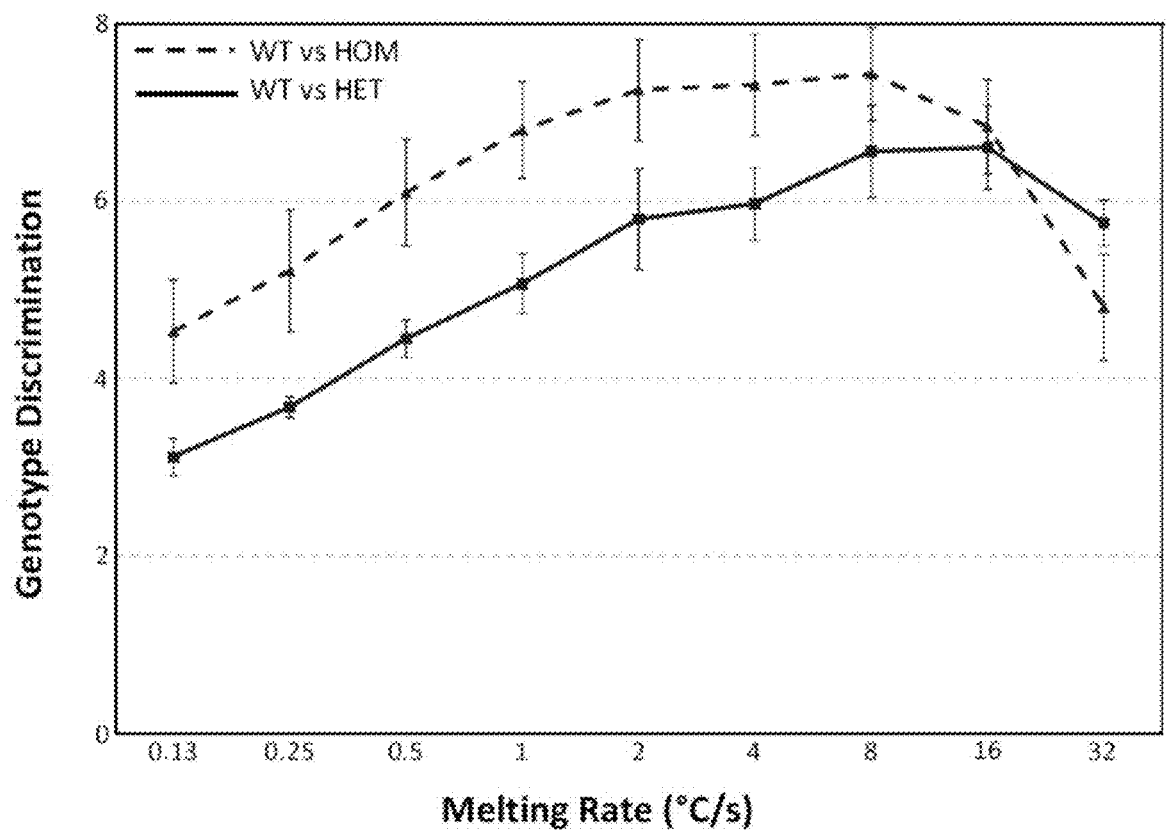
FIG. 15 demonstrates melting rate dependence of genotype discrimination.

FIG. 15 illustrates genotype discrimination as a function of melting rate. Genotype discrimination ratios of inter-class to intra-class distances were used to quantify the ease of classifying genotypes. The inter-class refers to differences between genotypes. The intra-class refers to differences between duplicates of same genotype. Wild-type vs homozygote (dashed line), and wild-type vs heterozygote (solid line) are shown. The distance between two curves is calculated by taking the mean of the absolute difference at each data point along x-axis (temperature). In FIG. 15 the data is also averaged across multiple targets (Factor 2, Factor 5, MTHFR 665, MTHFR 1286) as well. Each point in FIG. 15 displays the mean (dimensionless) discrimination ratio obtained from two investigators analyzing all four loci in eight cartridge runs for each melting rate. All four genotyping loci (MTHFR 665, Factor 2, Factor 5, and MTHFR 1286) were included in the data to best display the effect of melting rate across loci, although absolute differences across the loci do increase the variance (error bars show the standard error of the mean).

For quantification, inter-class differences were calculated by averaging all pairwise comparisons included in the inter-class calculation. For example, the four pairwise differences between the two wild-type and two heterozygous samples on each eight-channel read were averaged to get the wild-type vs heterozygous inter-class difference. For intra-class differences, the distance between all pairwise curves within each genotype involved were averaged. In one embodiment, a total of 1728 melting curves were acquired (eight cartridge runs of three genotypes in duplicate at four loci at nine melting rates) of which five (0.3%) were excluded from analysis (bubbles or irregular melting curves due to cartridge or fluidic control issues). The excluded samples were one curve at 0.13° C./s and two curves at both 1° C./s and 2° C./s rates. Custom software was used to perform the calculations.

Using a one-tailed t-test and assuming unequal variance, genotype discrimination between 0.13° C. and 8° C. is significantly different for homozygotes (p=0.005) and heterozygotes (p=0.0004). P is a probability value. If probability, p, that the homozygous mutation is significantly different from wild type and also the probability that the heterozygous mutation is significantly different from wild type. Both probability values p are less than 0.05 then, saying that the difference is significant and real, supporting the fact that genotypes can be differentiated.

According to one aspect of the invention, genotypes are classified by using inter-class and intra-class distance thresholds for the melting rate being used. One can expand high-likelihood classification regions according to melting rate, and obtain higher sensitivity and specificity by doing so. The optimal melting rate used maximizes the ratio of inter-class to intra-class distance, which minimizes the number of no-call samples as well as the number of false positive and false negative samples among those called. Melting curves are sequentially obtained for the one or more nucleic acid samples at a plurality of ramp rates in a specific interval to determine an optimal melting rate corresponding to the highest genotype discrimination, the genotype discrimination being calculated for each ramp rate in the interval. The optimal ramp rate maximizes the ratio of inter-class to intra-class distance, which minimizes the number of no-call samples and the number of false positive and false negative samples among those called.

Based on FIG. 15, the best discrimination of homozygotes occurs at rates of 2-8° C./s, while heterozygotes are best discriminated at 8-16° C./s. There was better discrimination between wild-type and homozygote than between wild-type and heterozygote, except at very high rates where data density was low. Accordingly, based on FIG. 15, with high speed melting, it is possible to achieve about a twofold increase in genotype discrimination.

In one non-limiting embodiment, all experiments were performed at two geographic sites. Two investigators, one from each site, analyzed all the data from the eight cartridge runs by manually-supervised, computer-assisted analysis using custom software written in LabView (National Instruments). Initial upper and lower temperature regions for background determination were automatically assigned by measuring the deviation of the melting signal from an exponential background. The inner temperatures for the melting curve region were set at 5% deviation and the outer limits defined a 2° C. interval for both upper and lower regions. These regions were manually reviewed and adjusted if necessary. The distance between two curves was taken as the absolute value of the maximum vertical distance between curves after background subtraction and normalization. To make this determination, all points collected within the melting region were used. This number varied with the melting rate (see Table 3).

Figure 16:
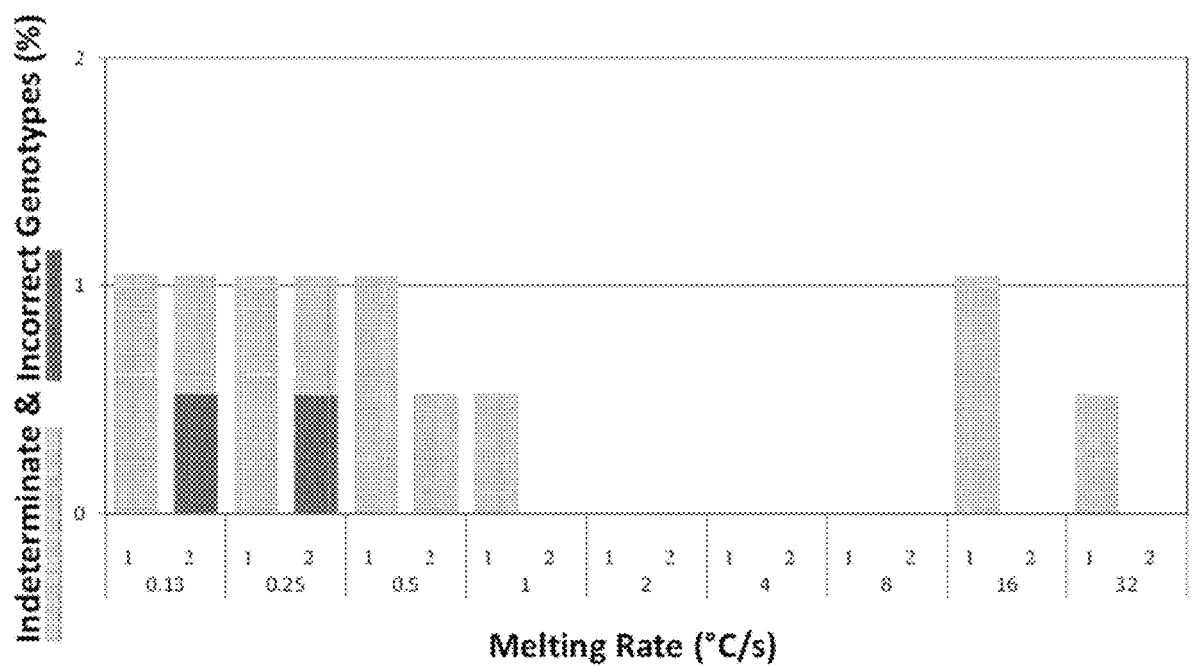
FIG. 16 is a histogram showing manual genotyping accuracy for different melting rates.

FIG. 16 demonstrates manual genotyping accuracy vs melting rate. For each of the nine melting rates, two investigators visually genotyped 192 melting curves or decided that they were not able to call the genotype (indeterminate).

The percentage of indeterminate and incorrect genotype calls for the first investigator (referred to as "1") and second investigator (referred to as "2") at each melting rate are shown. All combined, there were 13 (0.4%) indeterminate and two (0.06%) incorrect genotype calls. In general agreement with the genotype discrimination ratio analysis, all genotyping calls at melting rates from 2-8° C./s were correct, both incorrect calls and 10 of 13 indeterminate calls occurred at rates from 0.13-1° C./s and the three remaining indeterminate calls occurred at rates from 16-32° C./s where data density could be a leading contributor to genotyping difficulty.

Specifically, the second investigator ("2") made 2 incorrect (0.1%) and 3 indeterminate calls (0.2%), while the other made no incorrect but 10 indeterminate (0.6%) calls, for an overall error rate of 0.06% and an indeterminate rate of 0.4%. All errors were made at rates less than 0.5° C./s, while 77% of the indeterminate calls were at or below 1° C./s, and 23% at rates at or above 16° C./s.

Figure 17:
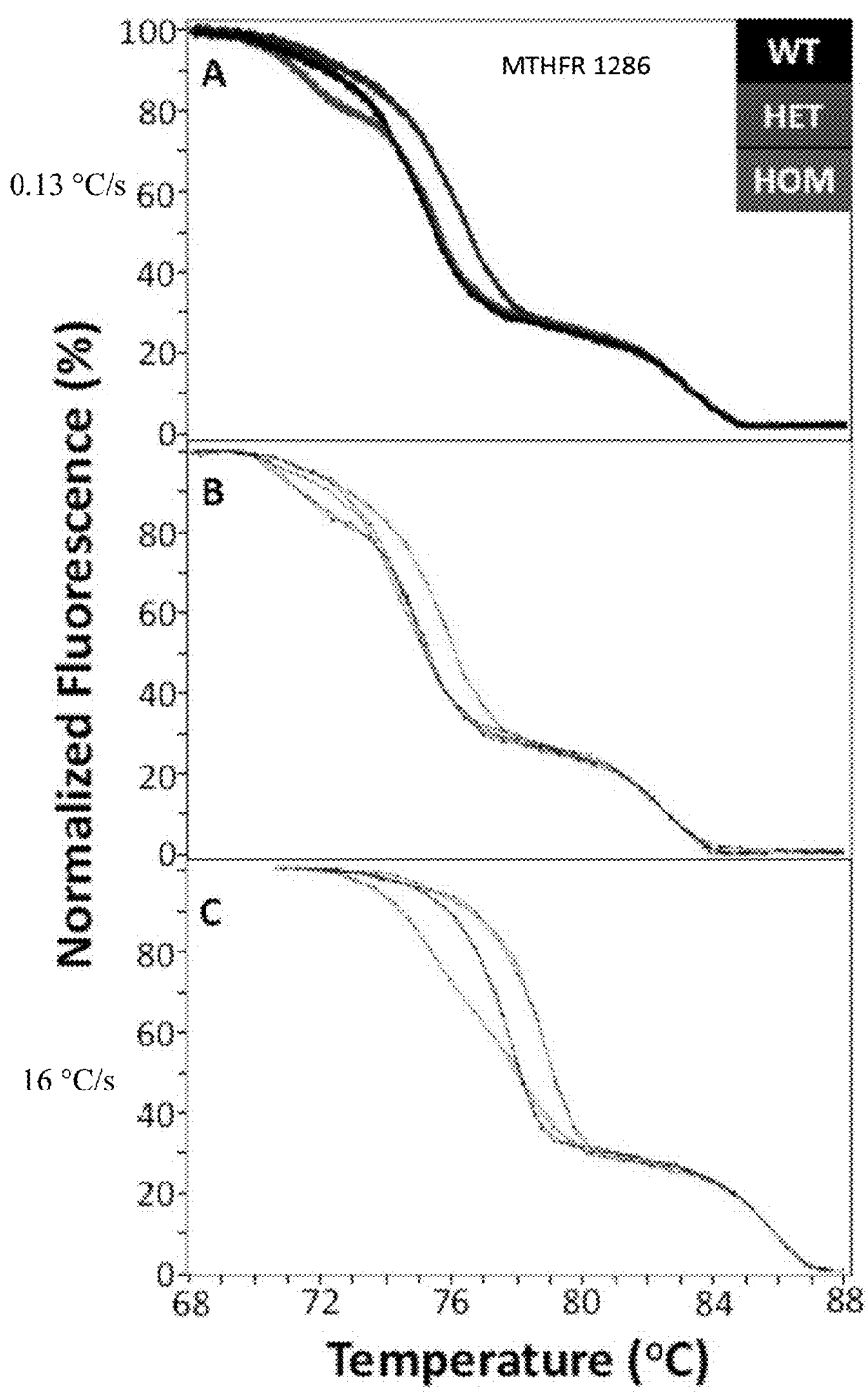
FIGS. 17A-C demonstrates the effects of melting rate and data density on melting curves. All melting data were acquired at 30 points per second, the maximum frequency supported by the hardware.

FIGS. 17A-C isolate the effects of melting rate and data density for MTHFR 1286 mutations. The influence of data density on MTHFR 1286 genotyping was explored by "thinning" a high density data set. Melting curves obtained at 0.13° C./s were converted to a low density data set equivalent to acquisition at 16° C./s. The thinned data did not group into genotypes as well as that acquired at 16° C./s, demonstrating that the higher melting rate accounted for the improvement in genotyping rather than the change in data density.

Specifically, all melting data were acquired at 30 points per second, the maximum frequency supported by the hardware. In FIG. 17A, at the slowest melting rate of 0.13° C./s, approximately 230 points are obtained per ° C. and the thick lines observed result from over-sampling and noise. At 32° C./s, genotype discrimination is degraded by under-sampling melting curve features (not shown). In FIG. 17B, the 0.13° C./s data from FIG. 17A is resampled at two points per ° C., the same rate at which the 16° C./s curves shown in FIG. 17C were acquired. Accordingly, at constant data density, the 16° C./s melting rate allows higher confidence genotyping than at 0.13° C./s.

Figure 18:
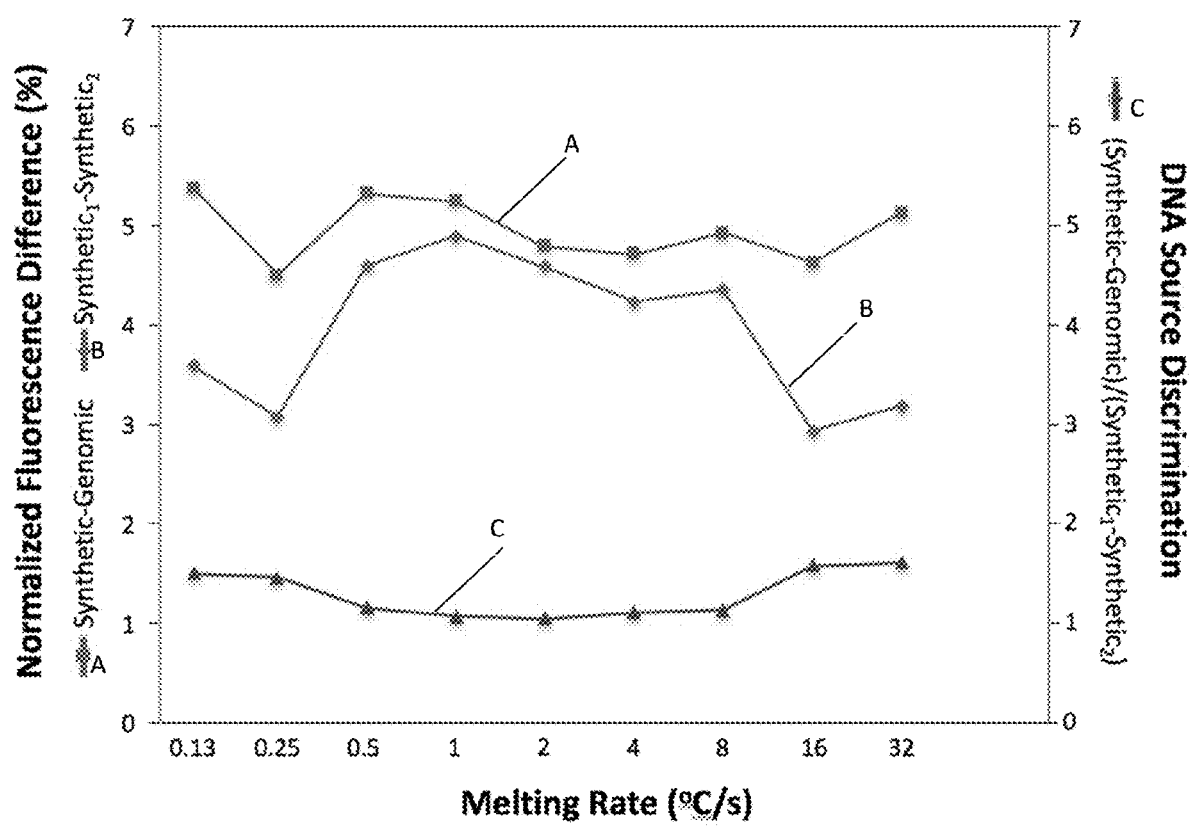
FIG. 18 demonstrates the normalized fluorescence difference for genomic and synthetic DNA as a function of melting rate.

FIG. 18 illustrates similarity between synthetic and genomic DNA (Factor 2, Factor 5, MTHFR 665, and MTHFR 1286) as templates for PCR and melting analysis in a single cartridge run. The DNA source discrimination ratio (C) is the mean distance from genomic DNA melting curves to synthetic melting curves (A) divided by the mean distance between synthetic melting curves (B). Data from one typical cartridge melting four target loci at nine exponentially increasing melting rates was used. The source discrimination ratio remains close to one across melting rates, suggesting that there is little difference between synthetic and genomic DNA in this analysis. Synthetic templates were used to limit DNA amplification variance, focus on the genotype resolution of melting, and have two of each genotype per locus on each cartridge run. Results obtained with synthetic templates were close to those with genomic DNA. Similarity was quantified using the discrimination ratio of distances between synthetic and genomic curves to distances between synthetic curves, which remained close to one.

FIGS. 19A-B illustrate similarity between accelerating and decelerating melting rates on different cartridge runs for Factor 2, Factor 5, MTHFR 665, MTHFR 1286 DNA. Melting curves on all cartridges were sequentially run at different melting rates on the same PCR products. Half of the cartridge runs were performed with increasing rates (0.13-32° C./s) and half with decreasing rates (32-0.13°/s). FIG. 19A separates the overall heterozygous vs wild type discrimination ratios (FIG. 15, solid line with squares) into contributions from increasing rate cartridges (line (1) with crosses) and decreasing rate cartridges (line (2) with triangles). FIG. 19B separates the homozygous mutant discrimination ratios (FIG. 15, broken line with triangles) into contributions from increasing rate cartridges (line (3) with circles) and decreasing rate cartridges (line (4) with asterisks). In both cases, genotype discrimination ratios increase with faster melting rates to a peak near 8° C./s before leveling or decreasing slightly at 16° C./s, and then decreasing at 32° C./s. Error bars are standard error of the mean. At the middle rate (2° C./s), the difference between curves in each panel is not significant (p=0.63 for heterozygotes and p=0.054 for homozygotes) suggesting little difference between accelerating and decelerating rates. P is the probability that there is a difference between running the test order slow to fast or fast to slow. The probability values, p, are both larger than 0.05 which means that there is no difference between order of running the melts. This shows that the data is not biased by the order in which the tests were run. When all genotype data from the four cartridges using accelerating rates were compared to the four using decelerating rates, similar genotype discrimination vs melting rate curves were observed. Both the heterozygous (FIG. 19A) and homozygous (FIG. 19B) discrimination ratios were similar in shape and peak around a melting rate of 8° C./s. Hence, for further analysis of the effect of rate on genotyping, both accelerating and decelerating cartridges were combined. Similarly, the overall effect of analyzer and location were combined because there were no apparent differences.

FIGS. 20A-B illustrates that the instrument measured melting temperature (Tm) increases with melting rates. In FIG. 20A, the wild-type melting temperatures (Tm) of each of the four loci obtained in one of the eight cartridge runs were plotted against the nine exponentially doubling melting rates. Each value was calculated as the average Tm of the melting curves of duplicate wild-type samples. These Tms are given by the maximum of the least-squares quadratic fit of the negative derivative peak after background removal, normalization, and temperature equalization of their internal temperature controls. In FIG. 20B, the wild-type Tm at 1° C./s (the melting rate used to calibrate the cartridge heaters) was subtracted from each Tm in FIG. 20A to observe the precise uniformity of the Tm increase across all loci up to the 2° C./s melting ramp rate, and the greater variability at higher rates. The loci were MTHFR 665 (green triangles), Factor 2 (blue diamonds), Factor 5 (red squares), and MTHFR 1286 (purple crosses).

The instrument measured Tm of each locus increased about 2.8° C. on average as the melting rate increased 250-fold from 0.13 to 32° C./s (FIGS. 20A-B). Increased variation occurred at 4° C./s and higher, perhaps because decreased data density affected the precision of the negative derivative peak fit. Genotyping was not affected by this Tm shift because all eight channels were affected equally; all genotype comparisons were made at specific rates. The effect of melting rate on genotyping the MTHFR 1286 locus from 0.13 to 32° C./s is shown in FIGS. 13A-I, taken from a representative cartridge run. Within each panel, a data set of two wild-type, two heterozygous, and two homozygous variant curves are shown. They are all aligned to the mean Tm of their internal temperature controls, seen as the rightmost peak in each curve. As the rates increased from 0.13 to 8° C./s, the heterozygote heteroduplex peaks increased and approached the homo duplex peaks in height and area, and the homozygous peaks became taller and thinner. From 8 to 32° C./s the two heterozygous peaks merged and the homozygous peaks became shorter and thicker, apparently because of low data density (<2 points/° C. at 16° C./s). Even at 32° C./s, the melting curves were still easily genotyped by visual inspection. Similar trends were seen for all four loci at melting rates of 0.13, 8, and 32° C./s (FIG. 14), where the internal temperature controls are not shown. For example, MTHFR 665 genotyping at 0.13° C./s had only a small heteroduplex peak. At 8° C., the heteroduplex contribution was much larger and, although it had merged into the homoduplex peak, genotyping was visually easier as confirmed by quantitative genotyping ratios that increased 1.9 fold between the 2 rates. That is, for heterozygote small amplicon genotyping, separation of the heteroduplex and homoduplex contributions into separate peaks was not as important as the separation of different genotypes.

Additional blinded studies were performed to explore the generality of the above observations to all classes of single nucleotide variants (SNVs) and to observe effects of GC content, homopolymer stretches, and amplicon length (See tables 4 and 5 in FIG. 21). Specifically, additional single nucleotide variant loci (table 5) were tested at rates from 0.13 to 32° C./s. Samples were PCR amplified from human genomic DNA or plasmids on a carousel LightCycler®v.1.5 using primers and conditions shown in Table 4. In one embodiment, PCR was performed in 10 μL volumes including 0.5 μmol/L of each primer, 0.4 U KlenTaq®1™ (Ab Peptides), 64 ng antiTaq antibody (eEnzyme), 3 mmol/L MgCl2, 50 mmol/L Tris (pH 8.5), 500 mg/L bovine serum albumin (Sigma), 1× LCGreen® Plus dye (BioFire Defense), and 200 μmol/L each dNTP. After amplification, samples were melted. This process limits any variation from PCR so that only the results of melting are tested.

There were no apparent differences between the SNV classes for heterozygous genotyping, although as expected, homozygotes were difficult to detect in SNVs. GC content varied between 39 and 65% with no apparent trend.

Observations of improved small amplicon genotyping at faster melting rates appeared to hold true for all SNV classes, different GC contents from 39-65%, and was not affected by homopolymer stretches. However, GC content and homopolymer stretches may have affected the ease of PCR amplification. Once adequately amplified, GC content and homopolymer stretches did not appear to adversely affect HSM. In contrast, PCR product length did affect the melting rate dependence of genotyping. For products 48-78 bp long in the blinded study, 92% of the heterozygote calls were correct, with the remaining 8% not called, all at the slowest speeds (0.13-0.25° C./s). For products 96-101 bp long, errors were made at both slow and fast speeds, with 5% no-calls at 0.13° C./s, and 2% no-calls and 1% miscalls at 32° C./s. With products 200-272 bp, many errors were made at fast speeds. Therefore, for small amplicons around 50 bp, faster melting improves genotyping. Faster melting was most beneficial with small amplicons around 50 bp. At 100 bp, melting rate did not appear to affect the ability to discriminate genotype, while at >200 bp, the trend was reversed and slower melting resulted in better genotyping.

The melting rates investigated here varied from 0.13 to 32° C./s with acquisition times from about 4 min to less than 1 s. Interestingly, with small amplicons, rare genotyping errors were only made at low rates rather than faster rates. That is, faster melting of small amplicons appears to achieve better melting, at least up to 8° C./s. Even at the fastest rate where the curves broaden because of low data density caused by a fixed camera frame rate, genotyping is still visually clear.

As the melting rate increases, heteroduplex peaks increase in height and area, making heterozygotes easier to identify. This can be rationalized by considering heteroduplexes in small amplicons as unstable, non-equilibrium duplexes that, over time, recombine to form the more stable, equilibrium homoduplexes. At slower rates, there is more time for recombination to occur at critical temperatures, and the observed heteroduplex peak diminishes. At faster rates, there is no time for recombination, and more heteroduplexes are observed. This explanation is consistent with prior observations (Wittwer et al., "High-resolution genotyping by amplicon melting analysis using LCGreen," Clin Chem 2003; 49:853-60). However, heteroduplexes in longer PCR products are less prone to recombine.

Rationalizing why faster rates improve genotyping of homozygotes in small amplicons is more difficult. As rates increase above 0.13° C./s, apparent Tms increase and derivative peaks amplified from homozygotes become sharper (taller and narrower), increasing the vertical separation between samples of different genotypes and the resulting discrimination ratio, thereby resulting in more distinct visual and quantitative genotyping. Perhaps the mechanism is also a non-equilibrium effect of strand disassociation vs association. The best rates for homozygote genotyping are 2-8° C./s, lower than the best rates for heterozygote (8-16° C./s), suggesting a unique mechanism.

Both homozygote and heterozygote discrimination degrade when the data density becomes low enough that melting features become obscured, particularly at 32° C./s. Faster data acquisition during melting may remove this limit, perhaps enabling even faster rates with even better genotype discrimination.

The genotyping improvement seen here with faster melting of small amplicons around 50 bp appears to generally apply to all types of SNVs. Although amplification of high or low GC content or homopolymer stretches may complicate PCR, if targets can be amplified, they can be genotyped by high speed melting. However, better results with faster rates may not apply to other melting applications that use larger amplicons greater than 100 bp such as heteroduplex scanning. Indeed, the genotyping improvement with faster rates decreased as the amplicons became larger, even reversing the trend with amplicons>200 bp.

Whatever the mechanism for improved genotyping of small amplicons at faster rates, the optimal rate of 8° C./s shared by both homozygous and heterozygous genotyping observed here will provide added value to extreme PCR. A protocol of 15-30 s of PCR followed by 4 s of melting would make point-of-care molecular diagnostics much more feasible (10× faster) than the same 15-30 s of PCR followed by 4 min of melting, even permitting reflex sequential testing on-site. For samples that do not require preparation before PCR, results should be available in less than 30 s. If sample preparation is required and such procedures can be completed in less than 30 s, a 1 min sample-to answer molecular diagnostic solution is enabled. As a final consideration, whenever a limit has been proposed (and widely accepted) for how fast PCR or melting can be performed, those limits have become obsolete over time.

Accordingly, microfluidics enables genotyping by melting analysis at rates up to 50° C./s, requiring less than is to acquire an entire melting curve. High speed melting reduces the time for melting analysis, decreases errors, and improves genotype discrimination of small amplicons. Combined with extreme PCR, high speed melting promises nucleic acid amplification and genotyping in less than one minute.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. A method for performing a nucleic acid high-speed melting analysis, the method comprising:
providing a microfluidic device having one or more nucleic acid samples therein;
providing an imaging system in communication with the one or more nucleic acid samples;
providing a thermal system in thermal communication with the one or more nucleic acid samples;
increasing the temperature of the one or more nucleic acid samples to achieve nucleic acid dissociation, wherein the temperature is increased by the thermal system at a ramp rate selected from a range of greater than 1° C./s to 50° C./s.
acquiring images of the one or more nucleic acid samples during nucleic acid dissociation to generate a melting profile for each nucleic acid sample; and
genotyping the nucleic acids based on the melting profile(s);
wherein genotypes are classified by using a discrimination value, wherein the discrimination value is calculated as a ratio of inter-class and intra-class distance for the melting rate being used, wherein the ratio is calculated as the mean of the absolute value of the difference between two inter-class curves at each value along the x-axis divided by the mean of the absolute value of the difference between two intra-class curves at each value along the x-axis; and wherein the inter-class distance reflects differences between genotypes and the intra-class distance reflects differences between duplicates of the same genotype.

2. The method of claim 1, wherein the microfluidic device comprises a microfluidic cartridge and a reaction chip.

3. The method of claim 2, wherein the reaction chip comprises one or more microchannels.

4. The method of claim 3, wherein the melting analysis is performed when the one or more samples are in the one or more microchannels of the reaction chip.

5. The method of claim 1, wherein the nucleic acid melting analysis is performed by increasing a temperature of the one or more nucleic acid samples at a rate selected from the range of greater than 1° C./s to 8° C./s.

6. The method of claim 1, wherein the nucleic acid melting analysis is performed by increasing a temperature of the one or more nucleic acid samples at a rate selected from the range of 8° C./s to 16° C./s.

7. The method of claim 1, wherein each of the nucleic acids in the one or more nucleic acid samples is less than 100 bp long.

8. The method of claim 1, wherein the microfluidic device is primed prior to performing the nucleic acid melting analysis.

9. The method of claim 1, wherein the nucleic acid melting analysis is preceded by amplification of the nucleic acids in the one or more nucleic acid samples.

10. The method of claim 1, wherein each of the one or more nucleic acid samples includes at least one internal temperature control sequence having a melting temperature that is substantially greater than a melting temperature of the nucleic acids in the one or more nucleic acid samples.

11. The method of claim 1, further comprising sequentially obtaining melting curves for the one or more nucleic acid samples at a plurality of ramp rates between 0.13° C./s and 32° C./s to determine an optimal ramp rate corresponding to the highest genotype discrimination, the genotype discrimination being calculated for the plurality of ramp rates between 0.13° C./s and 32° C./s.

12. The method of claim 1, wherein the ramp rate used maximizes the ratio of inter-class to intra-class distance, which minimizes the number of no-call samples and the number of false positive and false negative samples among those called.

13. The method of claim 12, wherein the ramp rate used results in a homozygote genotype discrimination value of greater than 6.

14. The method of claim 12, wherein the ramp rate used results in a heterozygote genotype discrimination value of greater than 5.

* * * * *